US008552256B2

(12) United States Patent
Takaiwa et al.

(10) Patent No.: US 8,552,256 B2
(45) Date of Patent: Oct. 8, 2013

(54) GENE CAPABLE OF BEING EXPRESSED SPECIFICALLY IN ENDOSPERM OF PLANT, PROMOTER FOR THE GENE, AND USE OF THE GENE AND THE PROMOTER

(75) Inventors: Fumio Takaiwa, Ibaraki (JP); Taiji Kawakatsu, Ibaraki (JP)

(73) Assignee: National Institute of Agrobiological Sciences, Tsukuba-shi, Ibaraki (JP)

( * ) Notice: Subject to any disclaimer, the term of this patent is extended or adjusted under 35 U.S.C. 154(b) by 184 days.

(21) Appl. No.: 12/936,718

(22) PCT Filed: Apr. 10, 2009

(86) PCT No.: PCT/JP2009/057311
§ 371 (c)(1),
(2), (4) Date: Dec. 14, 2010

(87) PCT Pub. No.: WO2009/125826
PCT Pub. Date: Oct. 15, 2009

(65) Prior Publication Data
US 2011/0093984 A1      Apr. 21, 2011

(30) Foreign Application Priority Data

Apr. 11, 2008   (JP) ................................ 2008-104132

(51) Int. Cl.
*C07K 14/415*   (2006.01)
*C12N 15/86*    (2006.01)

(52) U.S. Cl.
USPC ........ 800/287; 800/298; 435/320.1; 435/419; 536/24.1

(58) Field of Classification Search
None
See application file for complete search history.

(56) References Cited

U.S. PATENT DOCUMENTS

| 5,516,668 | A  | 5/1996 | Maruta |
| 6,576,815 | B1 | 6/2003 | Higo et al. |
| 6,576,820 | B1 | 6/2003 | Takaiwa et al. |
| 6,653,459 | B1 | 11/2003 | Von Schaewen |
| 6,924,097 | B1 | 8/2005 | Ohba et al. |
| 7,132,292 | B2 | 11/2006 | Komatsu et al. |
| 7,473,825 | B2 | 1/2009 | Takaiwa et al. |
| 7,728,191 | B2 | 6/2010 | Kuroda |
| 2004/0123343 | A1 | 6/2004 | La Rosa et al. |
| 2006/0277628 | A1 | 12/2006 | Sosa et al. |
| 2007/0136896 | A1 | 6/2007 | Takaiwa et al. |

FOREIGN PATENT DOCUMENTS

| EP | 1 264 886 A1 | 12/2002 |
| JP | 6-506584 A | 7/1994 |
| JP | 10-504969 A | 5/1998 |
| JP | 10-248570 A | 9/1998 |
| JP | 10-513364 A | 12/1998 |
| JP | 11-510056 A | 9/1999 |
| JP | 2000-41688 A | 2/2000 |
| JP | 3030339 B2 | 4/2000 |
| JP | 2000-507108 A | 6/2000 |
| JP | 3149951 B2 | 3/2001 |
| JP | 2001-169790 A | 6/2001 |
| JP | 2001-512318 A | 8/2001 |
| JP | 2001-512322 A | 8/2001 |
| JP | 2001-292777 A | 10/2001 |
| JP | 2001-517434 A | 10/2001 |
| JP | 2001-518305 A | 10/2001 |
| JP | 2001-519659 A | 10/2001 |
| JP | 2002-58492 A | 2/2002 |
| JP | 2002-504336 A | 2/2002 |
| JP | 2002-509696 A | 4/2002 |
| JP | 2002-209462 A | 7/2002 |
| JP | 2002-521072 A | 7/2002 |
| JP | 2002-253262 A | 9/2002 |
| JP | 2002-291484 A | 10/2002 |
| JP | 2002-539824 A | 11/2002 |
| JP | 2003-503033 A | 1/2003 |
| JP | 2003-510040 A | 3/2003 |
| JP | 2003-523172 A | 8/2003 |
| JP | 2004-500885 A | 1/2004 |
| JP | 2004-508803 A | 3/2004 |
| JP | 2004-105030 A | 4/2004 |
| JP | 2004-528022 A | 9/2004 |
| JP | 2004-321079 A | 11/2004 |
| JP | 2004-337004 A | 12/2004 |
| JP | 2005-27654 A | 2/2005 |
| JP | 2005-168500 A | 6/2005 |
| JP | 2006-512067 A | 4/2006 |
| JP | 2006-521107 A | 9/2006 |
| WO | WO 92/18634 A1 | 10/1992 |
| WO | WO 93/19189 A1 | 9/1993 |

(Continued)

OTHER PUBLICATIONS

Daniell, H., et al., "Medical molecular farming: production of antibodies, biopharmaceuticals and edible vaccines in plants," *TRENDS in Plant Science* 6:219-226, Elsevier Science Ltd., England (2001).
Fischer, R., et al., "Plant-based production of biopharmaceuticals," *Curr. Op. Plant Biol.* 7:152-158, Elsevier Ltd., England (2004).
Hartmann, R. and Meisel, H., "Food-derived peptides with biological activity: from research to food applications," *Curr. Op. Biotechnol.* 18:163-169, Elsevier Ltd., England (2007).
Kawakatsu, T., et al., "Characterization of a new rice glutelin gene *GluD-1* expressed in the starchy endosperm," *J. Exp. Botany* 59:4233-4245, Oxford Journals Open Access, England (2008).
Paine, J.A., et al., "Improving the nutritional value of Golden Rice through increased pro-vitamin A content," *Nature Biotechnol.* 23:482-487, Nature Publishing Group, England (2005).

(Continued)

*Primary Examiner* — Shubo (Joe) Zhou
*Assistant Examiner* — Russell Boggs
(74) *Attorney, Agent, or Firm* — Sterne, Kessler, Goldstein & Fox P.L.L.C.

(57) ABSTRACT

The present inventors identified a novel rice glutelin gene, GluD-1, which is expressed specifically in seeds. The promoter of the GluD-1 gene was confirmed to induce seed-specific gene expression, and to induce expression of downstream genes specifically in the endosperm during the early stage of seed maturation process. More specifically, the GluD-1 promoter can induce strong expression of an exogenous gene in sites including the endosperm.

24 Claims, 6 Drawing Sheets

(56) References Cited

FOREIGN PATENT DOCUMENTS

| WO | WO 96/07313 A1 | 3/1996 |
| --- | --- | --- |
| WO | WO 96/24679 A1 | 8/1996 |
| WO | WO 96/30509 A1 | 10/1996 |
| WO | WO 97/05261 A1 | 2/1997 |
| WO | WO 97/35983 A2 | 10/1997 |
| WO | WO 98/36085 A1 | 8/1998 |
| WO | WO 98/37211 A1 | 8/1998 |
| WO | WO 98/42851 A1 | 10/1998 |
| WO | WO 99/15642 A1 | 4/1999 |
| WO | WO 99/16890 A2 | 4/1999 |
| WO | WO 99/42589 A2 | 8/1999 |
| WO | WO 00/07431 A1 | 2/2000 |
| WO | WO 00/58352 A2 | 10/2000 |
| WO | WO 00/58453 A2 | 10/2000 |
| WO | WO 00/58454 A1 | 10/2000 |
| WO | WO 00/78985 A1 | 12/2000 |
| WO | WO 01/21644 A2 | 3/2001 |
| WO | WO 01/31018 A1 | 5/2001 |
| WO | WO 01/40440 A2 | 6/2001 |
| WO | WO 01/64865 A1 | 9/2001 |
| WO | WO 01/98509 A2 | 12/2001 |
| WO | WO 02/064814 A2 | 8/2002 |
| WO | WO03-008540 * | 1/2003 |
| WO | WO 03/008540 A2 | 1/2003 |
| WO | WO 2004/056993 A1 | 7/2004 |
| WO | WO 2004/085656 A2 | 10/2004 |

OTHER PUBLICATIONS

Qu, L.Q., and Takaiwa, F., "Evaluation of tissue specificity and expression strength of rice seed component gene promoters in transgenic rice," *Plant Biotechnol. J.* 2:113-125, Blackwell Publishing Ltd, England (2004).

Storozhenko, S., et al., "Folate fortification of rice by metabolic engineering," *Nature Biotechnol.* 25:1277-1279, Nature Publishing Group, England (2007).

Takagi, H., et al., "A rice-based edible vaccine expressing multiple T cell epitopes induces oral tolerance for inhibition of Th2-mediated IgE responses," *Proc. Natl. Acad. Sci. USA* 102:17525-17530, The National Academy of Sciences of the USA, United States (2005).

Takagi, H., et al., "Oral immunotherapy against a pollen allergy using a seed-based peptide vaccine," *Plant Biotechnol. J.* 3:521-533, Blackwell Publishing Ltd., England (2005).

Takaiwa, F., et al., "Endosperm tissue is good production platform for artificial recombinant proteins in transgenic rice," *Plant Biotechnol. J.* 5:84-92, Blackwell Publishing Ltd., England (2007).

Wu, C.-Y., et al., "Promoters of Rice Seed Storage Protein Genes Direct Endosperm-Specific Gene Expression in Transgenic Rice," *Plant Cell Physiol. 39*:885-889, Japanese Society of Plant Physiologists, Japan (1998).

Ye, X., et al., "Engineering the Provitamin A (β-Carotene) Biosynthetic Pathway into (Carotenoid-Free) Rice Endosperm," *Science 287*:303-305, American Association for the Advancement of Science, United States (2000).

NCBI GenBank Accession No. EF122464, Yoon, U.H., et al., Entry Date Dec. 19, 2006.

NCBI GenBank Accession No. AY429650, Wan, J.M., et al., Entry Date Nov. 1, 2003.

International Search Report for International Application No. PCT/JP2009/057311, Japanese Patent Office, Japan, mailed Jun. 2, 2009.

Unverified English language translation of Japanese Patent Publication No. 10-248570 A, published Sep. 22, 1998, Japanese Patent Office, Patent Abstracts of Japan.

Unverified English language translation of Japanese Patent Publication No. 2000-041688 A, published Feb. 15, 2000, Japanese Patent Office, Patent Abstracts of Japan.

Unverified English language translation of Japanese Patent Publication No. 2001-292777 A, published Oct. 23, 2001, Japanese Patent Office, Patent Abstracts of Japan.

Unverified English language translation of Japanese Patent Publication No. 2002-209462 A, published Jul. 30, 2002, Japanese Patent Office, Patent Abstracts of Japan.

Unverified English language translation of Japanese Patent Publication No. 2002-253262 A, published Sep. 10, 2002, Japanese Patent Office, Patent Abstracts of Japan.

Unverified English language translation of Japanese Patent Publication No. 2002-291484 A, published Oct. 8, 2002, Japanese Patent Office, Patent Abstracts of Japan.

Unverified English language translation of Japanese Patent Publication No. 2004-105030 A, published Apr. 8, 2004, Japanese Patent Office, Patent Abstracts of Japan.

Unverified English language translation of Japanese Patent Publication No. 2005-027654 A, published Feb. 3, 2005, Japanese Patent Office, Patent Abstracts of Japan.

* cited by examiner

| | | |
|---|---|---|
| NIPPONBARE | 1 | MATTTSLLSSCLCALLLAPLFSQGVDAWESRQGASRQCRFDRLQAFEPLRKVRSEAGDTEYFDERNEQFRCAGVFVIRRVIEPQGLVVPRYSNTPALAYIIQGKGYVGLT |
| WATARIBUNE 2 | 1 | MATTTSLLSSCLCALLLAPLFSQGVDAWESRQGASRQCRFDRLQAFEPLRKVRSEAGVTEYFDERNEQFRCAGVFVIRRVIEPQGLVVPRYSNTPALAYIIQGKGYVGLT |
| KASALATH | 1 | MATTTSLLSSCLCALLLAPLFSQGVDAWESRQGASRECRFDRLQAFEPLRKARSEAGVTEYFDERNEQFRCAGVFVIRRVIEPQGLVVPRYSNTPALAYIIQGKGYVGLT |
| NONA BOKRA | 1 | MATTTSLLSSCLCALLLAPLFSQGVDAWESRQGASRQCRFDRLQAFEPLRKARSEAGVTEYFDEINEQFRCAGVFVIRRVIEPQGLVVPRYSNTPALAYIIQGKGYVGLT |
| CONSENSUS | 1 | ************************************ *****:**** :******************************* |
| NIPPONBARE | 111 | FPGCPATHQQQFQLFEQRQSDQAHKFRDEHQKIHEFRQGDVVALPASVAHWFYNGGDTPAVVYVYDIKSFANQLEPRQKEFLLAGNNQRGQQIFEHSIFQHSGQNIFSG |
| WATARIBUNE 2 | 111 | FPGCPATHQQQFQLFEQRQSDQAHKFRDEHQKIHEFRQGDVVALPASVAHWFYNGGDTPAVVYVYDIKSFANQLEPRQKEFLLAGNNQRGQQIFEHSIFQHSGQNIFSG |
| KASALATH | 111 | FPGCPATHQQQFQLFEQRQSDQAHKFRDEHQKIHEFRQGDVVALPASVAHWFYNGGDTPAVVYVYDIKSFANQLEPRQKEFLLAGNNQRGQQIFEHSIFQHSGQNIFSG |
| NONA BOKRA | 111 | FPGCPATHQQQFQLFEQRQSDQAHKFRDEHQKIHEFRQGDVVALPASVAHWFYNGGDTPAVVYVYDIKSFANQLEPRQKEFLLAGNNQRGQQIFEHSIFQHSGQNIFSG |
| CONSENSUS | 111 | **************************************************************************************************** |
| NIPPONBARE | 221 | FNTEVLSEALGINTEASKRLQSNDQRGDIIRVKHGLQLLKPTLTQRQEERQYQVQYREGQYNGLDENFCTIKARVNIENPSRADYYNPRAGRITLLNNQKFPILNL |
| WATARIBUNE 2 | 221 | FNTEVLSEALGINTEASKRLQSNDQRGDIIRVKHGLQLLKPTLTQRQEEHRQYQVQYREGQYNGLDENFCTIKARVNIENPSRADYYNPRAGRITLLNNQKFPILNL |
| KASALATH | 221 | FNTEVLSEALGINTEAAKRLQSNDQRGDIIRVKHGLQLLKPTLTQRQEEPRQYQVQYREGQYNGLDENFCTIKARVNIENPNRADYYNPRAGRITLLNNQKFPILNL |
| NONA BOKRA | 221 | FNTEVLSEALGINTEAAKRLQSNDQRGDIIRVKHGLQLLKPTLTQRQEEPRQYQVQYREGQYNGLDENFCTIKARVNIENPNRADYYNPRAGRITLLNNQKFPILNL |
| CONSENSUS | 221 | **************:****************************:***********************:****************** |
| NIPPONBARE | 331 | GMGAARVNLYQNALLSPFWNINAHSVVYIIQGSVRVQVANNQGRSVFNGVLHQGQLLIIPQNHAVIKKAEHNGCQYVAIKTISDPTVSMVAGKNSILRALPVDVIANAYR |
| WATARIBUNE 2 | 331 | GMGAARVNLYQNALLSPFWNINAHSVVYIIQGSVRVQVANNQGRSVFNGVLHQGQLLIIPQNHAVIKKAEHNGCQYVAIKTISDPTVSMVAGKNSILRALPVDVIANAYR |
| KASALATH | 331 | GMGAARVNLYQNALLSPFWNINAHSVVYIIQGSAQVQVANNQGRTVFSMVLHQGQLLIIPQNHAVIKKAEHNGCQYVAIKTIPNPMVSRVAGKNSILRALPVDVIANAYR |
| NONA BOKRA | 331 | GMGAARVNLYQNALLSPFWNINAHSVVYIIQGSAQVQVANNQGRTVFSMVLHQGQLLIIPQNHAVIKKAEHNGCQYVAIKTIPNPMVSRVAGKNSILRALPVDVIANAYR |
| CONSENSUS | 331 | *******************************: ****:. ************************:*:.:******************* |
| NIPPONBARE | 441 | ISRDEARRLKNNRADEIGPFTPRFPQKSQRGYQFLTEGLSLIGM (SEQ ID NO: 8) |
| WATARIBUNE 2 | 441 | ISRDEARRLKNNRADEIGPFTPRFPQKSQRGYQFLTEGLSLIGM (SEQ ID NO: 9) |
| KASALATH | 441 | ISRDEARRLKNNRADEIGAFTPRFPQKSQRGYQFLTKGLSLIGM (SEQ ID NO: 10) |
| NONA BOKRA | 441 | ISRDEARRLKNNRADEIGAFTPRFPQKSQRGYQFLTKGLSLIGM (SEQ ID NO: 11) |
| CONSENSUS | 441 | ****************.************:***** |

FIG. 4

GENE CAPABLE OF BEING EXPRESSED SPECIFICALLY IN ENDOSPERM OF PLANT, PROMOTER FOR THE GENE, AND USE OF THE GENE AND THE PROMOTER

TECHNICAL FIELD

The present invention relates to a gene expressed specifically in the endosperm of a plant, a promoter of the gene, and use thereof.

BACKGROUND ART

As an energy source for germination to leaf production until rice is capable of carrying out photosynthesis, large quantities of protein, starch, and lipid are accumulated in the albumen tissue of rice seeds. These accumulated materials are very stable, and germination is possible even after a few years of storage at ordinary temperature. Accumulated findings on gene expression regulatory mechanisms and advancement in genetic recombination techniques have lead to many efforts in recent years on the accumulation of useful substances in the seeds of plants (see Non-patent Documents 1 to 3).

Genetic recombination techniques may also be used to produce useful substances in microorganisms or animals, but the use of plants has many advantages (see Non-patent Documents 1 and 2). For example, since plants produce energy by using sun light and carbon dioxide in the atmosphere, they do not consume fossil fuels or pollute the atmosphere, and are benign to the earth's resources and environment. Furthermore, plants represented by rice are highly safe because they do not contain harmful substances to humans such as prions, viruses typical of animals, and toxins of microorganisms in the first place. Furthermore, the cost when using plants is estimated to be only one-tenth to one-fiftieth compared to when using microorganisms or animals. Thus, use of plants is very advantageous.

Because of such advantages, development of second-generation genetically modified crops that contain useful substances with health-related functions is promoted in recent years by using genetic recombination techniques. Known representative examples include cedar pollen allergy-relieving rice in which part of the cedar pollen antigen recognition site (epitope) is expressed in the rice albumen (see Non-patent Documents 4 and 5), and golden rice in which β-carotene is highly accumulated by expressing enzymes derived from maize and bacteria in the rice albumen (see Non-patent Documents 6 and 7).

As described above, plants are recognized for their potential as bioreactors; thus, development of third-generation genetically modified crops that accumulate raw materials of pharmaceuticals such as antibodies or vaccines is expected. Producing useful substances less expensively and in large amounts is very important in advancing the actual realization of third-generation genetically modified crops.

There are multiple factors that determine the amount of exogenous gene products, and the most important factor is expression promoter. This is because the timing, site, and/or amount of exogenous gene expression are regulated by the expression promoter. When rice is used as a host, the exogenous gene products are known to accumulate in larger amount in the albumen rather than in the assimilatory tissues such as leaves and stems (see Non-patent Document 8). Furthermore, it is known that in some cases expression of exogenous genes in leaves, stems, and such has harmful effects on growth. Accordingly, promoters that cause high expression of exogenous genes specifically in the albumen are considered to be useful, and many promoters that induce albumen-specific expression have been isolated and used.

So far, for example, the GluA-2 promoter and GluB-1 promoter have been commonly used as rice-seed-specific expression-inducing promoters (see Non-patent Documents 4 and 6). However, these promoters induce expression mainly in small regions in the outermost layers of the albumen called aleuron layer and subaleurone layer (see Non-patent Document 9).

On the other hand, the Glb-1 promoter, 20 kDa globulin, and 16 kDa allergen promoter are known as promoters that induce expression in internal endosperm; however, because they induce expression in places other than the seed, and induce expression during the vegetative growth stage in addition to the stage of seed formation, they could not be used for induction of exogenous genes that cause growth inhibition. Furthermore, there are problems such as weak promoter activity and their use has been limited (see Non-patent Documents 10 and 11).

Prior art documents relating to the present invention are shown below.

[Prior Art Documents]
[Patent Documents]
[Patent Document 1] Japanese Patent Application Kokai Publication No. (JP-A) 2004-321079 (unexamined, published Japanese patent application)
[Patent Document 2] JP-A (Kokai) 2002-209462
[Patent Document 3] JP-A (Kokai) 2002-058492
[Patent Document 4] Japanese Patent Kohyo Publication No. (JP-A) 2006-521107 (unexamined Japanese national phase publication corresponding to a non-Japanese international publication)
[Patent Document 5] JP-A (Kohyo) 2006-512067
[Patent Document 6] JP-A (Kohyo) 2004-528022
[Patent Document 7] JP-A (Kohyo) 2003-503033
[Patent Document 8] JP-A (Kohyo) 2002-539824
[Patent Document 9] JP-A (Kohyo) 2001-518305
[Patent Document 10] JP-A (Kohyo) H10-513364
[Patent Document 11] Japanese Patent Saikohyo Publication No. (JP-A) 2004/056993 (unexamined Japanese national phase publication corresponding to a Japanese international publication)
[Patent Document 12] Japanese Patent No. 3149951
[Patent Document 13] Japanese Patent No. 3030339
[Patent Document 14] JP-A (Saikohyo) 01/064865
[Patent Document 15] JP-A (Kohyo) H11-510056
[Patent Document 16] JP-A (Saikohyo) 96/030509
[Patent Document 17] JP-A (Kohyo) H06-506584
[Patent Document 18] JP-A (Kokai) 2002-291484
[Patent Document 19] JP-A (Kokai) 2002-253262
[Patent Document 20] JP-A (Kohyo) 2004-500885
[Patent Document 21] JP-A (Kohyo) 2004-508803
[Patent Document 22] JP-A (Kohyo) 2003-523172
[Patent Document 23] JP-A (Saikohyo) 00/058454
[Patent Document 24] JP-A (Kohyo) 2002-521072
[Patent Document 25] JP-A (Kohyo) 2002-504336
[Patent Document 26] JP-A (Kohyo) 2001-512318
[Patent Document 27] JP-A (Kokai) 2005-168500
[Patent Document 28] JP-A (Kokai) 2005-027654
[Patent Document 29] JP-A (Kokai) 2004-105030
[Patent Document 30] JP-A (Kokai) 2001-292777
[Patent Document 31] JP-A (Kokai) 2001-169790
[Patent Document 32] JP-A (Kohyo) 2003-510040
[Patent Document 33] JP-A (Kokai) 2000-041688
[Patent Document 34] JP-A (Kohyo) 2002-509696
[Patent Document 35] JP-A (Kohyo) 2001-517434
[Patent Document 36] JP-A (Kohyo) 2001-519659

[Patent Document 37] JP-A (Kokai) H10-248570
[Patent Document 38] JP-A (Kohyo) 2001-512322
[Patent Document 39] JP-A (Kohyo) 2000-507108
[Patent Document 40] JP-A (Kohyo) H10-504969
[Non-Patent Documents]
[Non-patent Document 1] Daniell, H. et al., "Medical molecular farming: production of antibodies, biopharmaceuticals and edible vaccines in plants", Trends Plant Sci, (2001), Vol. 6, p. 219-226.
[Non-patent Document 2] Fischer, R. et al., "Plant-based production of biopharmaceuticals", Curr Opin Plant Biol, (2004), Vol. 7, p. 152-158.
[Non-patent Document 3] Hartmann, R. and Meisel, H., "Food-derived peptides with biological activity: from research to food applications", Curr Opin Biotechnol, (2007), Vol. 18, p. 163-169.
[Non-patent Document 4] Takagi, H. et al., "A rice-based edible vaccine expressing multiple T cell epitopes induces oral tolerance for inhibition of Th2-mediated IgE responses", Proc Natl Acad Sci USA, (2005a), Vol. 102, p. 17525-17530.
[Non-patent Document 5] Takagi, H. et al., "Oral immunotherapy against a pollen allergy using a seed-based peptide vaccine", Plant Biotechnol J, (2005b), Vol. 3, p. 521-533.
[Non-patent Document 6] Paine, J. et al., "Improving the nutritional value of Golden Rice through increased provitamin A content", Nat Biotechnol, (2005), Vol. 23, p. 482-487.
[Non-patent Document 7] Ye, X. et al., "Engineering the provitamin A (beta-carotene) biosynthetic pathway into (carotenoid-free) rice endosperm", Science, (2000), Vol. 287, p. 303-305.
[Non-patent Document 8] Takaiwa, F. et al., "Endosperm tissue is good production platform for artificial recombinant proteins in transgenic rice", Plant Biotechnol J, (2007), Vol. 5, p. 84-92.
[Non-patent Document 9] Qu, I. Q. and Takaiwa, F., "Evaluation of tissue specificity and expression strength of rice seed component gene promoters in transgenic rice", Plant Biotechnol J, (2004), Vol. 2, p. 113-125.
[Non-patent Document 10] Storozhenko, S. et al., "Folate fortification of rice by metabolic engineering", Nat Biotechnol, (2007), Vol. 25, p. 1277-1279.
[Non-patent Document 11] Wu, C. Y. et al., "Promoters of rice seed storage, protein genes direct endosperm-specific gene expression in transgenic rice", Plant and Cell Physiology, (1998), Vol. 39, p. 885-889.

SUMMARY OF THE INVENTION

Problems to be Solved by the Invention

An objective of the present invention is to provide a gene that is expressed specifically in the endosperm of a plant, a promoter of the gene, and use thereof.

Means for Solving the Problems

To modify the albumen components by causing production of useful substances such as functional components or vaccines in the seed albumen, the edible part of rice, using genetic recombination techniques, a promoter that induces gene expression specifically in tissues including the albumen is necessary. So far, various types of seed storage protein gene promoters have been isolated as albumen-specific promoters.

However, as described above, many of these promoters are those inducing expression in small areas of the aleurone layer and subaleurone layer.

The present inventors carried out a dedicated study as described below to solve the above-mentioned objective.

The present inventors identified a novel rice glutelin gene GluD-1 which is expressed specifically in seeds. When a construct in which a promoter of the GluD-1 gene (hereinafter, this may be referred to as a GluD-1 promoter) and the β-glucuronidase (GUS) gene are linked was introduced into rice, the GluD-1 promoter induced seed-specific gene expression, and induced endosperm-specific expression of downstream genes during the early stage of seed maturation process. Since GluD-1 can be confirmed by CBB staining of SDS-PAGE of proteins extracted from rice seeds, the GluD-1 promoter was considered to induce sufficiently strong expression.

As described above, the GluD-1 promoter of the present invention is a promoter that induces exogenous gene expression specifically in the endosperm, and in the early stage of seed maturation, it enables induction of high expression of exogenous genes in the endosperm which constitutes a large portion of the albumen in a complementary manner with other glutelin genes. That is, unlike the conventionally used promoters, use of a GluD-1 promoter to induce exogenous gene expression enables elevated and specific expression of useful substances in tissues including a large area, the endosperm.

Therefore, as a promoter that induces exogenous gene expression specifically in the endosperm, the GluD-1 promoter of the present invention is considered to be useful.

Specifically, the present invention relates to a gene expressed specifically in the endosperm of a plant seed, a promoter of the gene, and use thereof.

[1] A DNA of any one of (a) to (d) below:
(a) a DNA comprising the nucleotide sequence of SEQ ID NO: 1;
(b) a DNA encoding the amino acid sequence of SEQ ID NO: 2;
(c) a DNA encoding a protein comprising an amino acid sequence with one or more amino acid substitutions, deletions, additions, and/or insertions in the amino acid sequence of SEQ ID NO: 2, and wherein the protein is functionally equivalent to a protein comprising the amino acid sequence of SEQ ID NO: 2; and
(d) a DNA that hybridizes under stringent conditions with a DNA comprising the nucleotide sequence of SEQ ID NO: 1, and encodes a protein functionally equivalent to a protein comprising the amino acid sequence of SEQ ID NO: 2;
[2] a DNA encoding an antisense RNA against a transcript of the DNA of [1] or a portion thereof;
[3] a DNA encoding an RNA that has ribozyme activity of specifically cleaving a transcript of the DNA of [1];
[4] a DNA encoding an RNA that has the function of inhibiting expression of the DNA of [1] by RNAi effect;
[5] a DNA encoding an RNA that suppresses expression of the DNA of [1] by co-suppression effect during expression in a plant cell;
[6] a DNA encoding a protein having a dominant negative phenotype of a protein encoded by the endogenous DNA of [1] in a plant cell;
[7] a protein encoded by the DNA of [1];
[8] a vector comprising the DNA of any one of [1] to [6];
[9] a transformed plant cell comprising the DNA of any one of [1] to [6], or the vector of [8];
[10] a transformed plant comprising the transformed plant cell of [9];

[11] a transformed plant which is a progeny or clone of the transformed plant of [10];

[12] a reproductive material of the transformed plant of [10] or [11];

[13] a DNA of any one of (a) to (c) below, which has promoter activity:

(a) a DNA comprising the nucleotide sequence of SEQ ID NO: 3;

(b) a DNA comprising a nucleotide sequence with one or more nucleotide substitutions, deletions, additions, and/or insertions in the nucleotide sequence of SEQ ID NO: 3, and which is functionally equivalent to the DNA comprising the nucleotide sequence of SEQ ID NO: 3; and (c) a DNA that hybridizes under stringent conditions with a DNA comprising the nucleotide sequence of SEQ ID NO: 3;

[14] the DNA of [13], which has plant endosperm-specific promoter activity;

[15] the DNA of [14], wherein the plant accumulates a seed storage protein;

[16] a DNA having a structure in which an exogenous gene is operably linked downstream of the DNA of any one of [13] to [15];

[17] a vector comprising the DNA of any one of [13] to [16];

[18] a transformed plant cell comprising the DNA of any one of [13] to [16] or the vector of [17];

[19] a transformed plant comprising the transformed plant cell of [18];

[20] a transformed plant which is a progeny or clone of the transformed plant of [19];

[21] a reproductive material of the transformed plant of [19] or [20];

[22] a method for producing a transformed plant, which comprises the step of introducing into a plant cell the DNA of any one of [1] to [6] and [13] to [16], or the vector of [8] or [17];

[23] a method for expressing an exogenous gene specifically in an endosperm of a plant, which comprises the step of introducing into a plant cell the DNA of any one of [13] to [16], or the vector of [17];

[24] a method for producing a transformed plant, wherein expression of the protein of [7] is inhibited by administration of the DNA of any one of [2] to [6], or a vector comprising the DNA of any one of [2] to [6];

[25] the method of [23] or [24], wherein the plant accumulates a seed storage protein;

[26] a plant obtained by the method of any one of [23] to [25], or a seed thereof;

[27] an agent for inducing expression of an exogenous gene specifically in an endosperm of a plant, which comprises (a) or (b) below as an active ingredient:

(a) the DNA of any one of [13] to [16]; or (b) the vector of [17];

[28] an agent for inducing accumulation of an exogenous protein specifically in an endosperm of a plant, which comprises (a) or (b) below as an active ingredient:

(a) the DNA of any one of [13] to [16]; or (b) the vector of [17]; and

[29] a method of screening for a candidate compound that regulates promoter activity of the DNA of any one of [13] to [16], wherein the method comprises the steps of:

(a) contacting a test compound with a cell or cell extract solution comprising a DNA having a structure in which a reporter gene is operably linked under the control of the DNA of any one of [13] to [16];

(b) measuring the expression level of the reporter gene; and (c) selecting a compound that changes the expression level of the reporter gene compared to that measured in the absence of the test compound.

Furthermore, the present invention provides:

[30] a method for inducing accumulation of an exogenous protein specifically in an endosperm of a plant, which comprises the step of introducing into a plant cell the DNA of any one of [13] to [16] or the vector of [17];

[31] use of the DNA of any one of [1] to [6] and [13] to [16], or the vector of [8] or [17] in producing a transformed plant;

[32] use of the DNA of any one of [13] to [16] or the vector of [17] in producing an agent for inducing expression of an exogenous gene specifically in an endosperm of a plant;

[33] use of the DNA of any one of [13] to [16] or the vector of [17] in producing an agent for inducing accumulation of an exogenous protein specifically in an endosperm of a plant;

[34] the DNA of any one of [13] to [16] or the vector of [17] for inducing expression of an exogenous gene specifically in an endosperm of a plant; and

[34] the DNA of any one of [13] to [16] or the vector of [17] for inducing accumulation of an exogenous protein specifically in an endosperm of a plant.

Effects of the Invention

Twenty-eight SNPs were detected between Nipponbare and Nona Bokra, and of them, 16 SNPs were those that produce amino acid substitutions (FIG. 4). This means that SNPs are present in a percentage of about 1.9% on average, and this value is higher than the SNP rate (0.7%) in the whole genome between rice cultivars (Nasu, S. et al., "Search for and analysis of single nucleotide polymorphisms (SNPs) in rice (*Oryza sativa, Oryza rufipogon*) and establishment of SNP markers", DNA Research, (2002), Vol. 9, p. 163-171). A region where many mutations and introduction of sequences of various sizes are tolerated is called a variable region and is known to exist in 11 S Globulin which is homologous to rice glutelin (Argos, P. et al., "Structural similarity between legumin and vicilin storage proteins from legume", EMBO Journal, (1985), Vol. 4, p. 1111-1117). In rice glutelin, three variable regions have been found to exist in the acidic subunit (Okita, T. et al., "Structure and expression of the rice glutelin multigene family.", J. Biol. Chem., (1989), Vol. 264, p. 12573-12581). Many of the mutations accompanying amino acid substitution in GluD-1 are present in the basic subunit. This indicates that the sequence of the basic subunit of GluD-1 has plasticity, and indicates that the amino acid composition in a rice seed may be modified by artificial amino acid substitution. Specifically, since the content of lysine, which is an essential amino acid, is low in rice seeds, the nutritional value of rice seeds may be increased by artificially introducing lysine into the basic subunit.

The GluD-1 promoter provided by the present invention induces seed-specific gene expression, and particularly induces expression in the endosperm in the early stage of seed ripening. Useful substances can be expressed in a large region called the endosperm by inducing exogenous gene expression using the GluD-1 promoter of the present invention. That is, the GluD-1 promoter of the present invention can be used as a tool for substance production in rice endosperm or modification of endosperm component by genetic recombination techniques. For example, since a large amount of starch, which not only becomes an energy source but also relates to taste, is included in the endosperm, various needs can be optimally met by regulating the metabolic pathway using the GluD-1 promoter provided by the present invention.

Furthermore, for example, in the case of white rice, by using the GluD-1 promoter of the present invention to induce endosperm-specific expression of exogenous genes and express useful substances, the possibility that the useful substance will be washed away when washing is low, and the useful substance can certainly be consumed. In addition, even if the rice is polished, loss of the useful exogenous gene products accumulated in the albumen will be small in proportion.

BRIEF DESCRIPTION OF THE DRAWINGS

FIG. 4 depicts a diagram which compares the GluD-1 amino acid sequences in Nipponbare, Wataribune 2, Kasalath, and Nona Bokra. The amino acids showing polymorphism are indicated by dots in the consensus row and also surrounded by box. The polymorphism detected between Nipponbare and Wataribune 2 is indicated by an asterisk (*) in the very top row.

MODE FOR CARRYING OUT THE INVENTION

Figure 1:
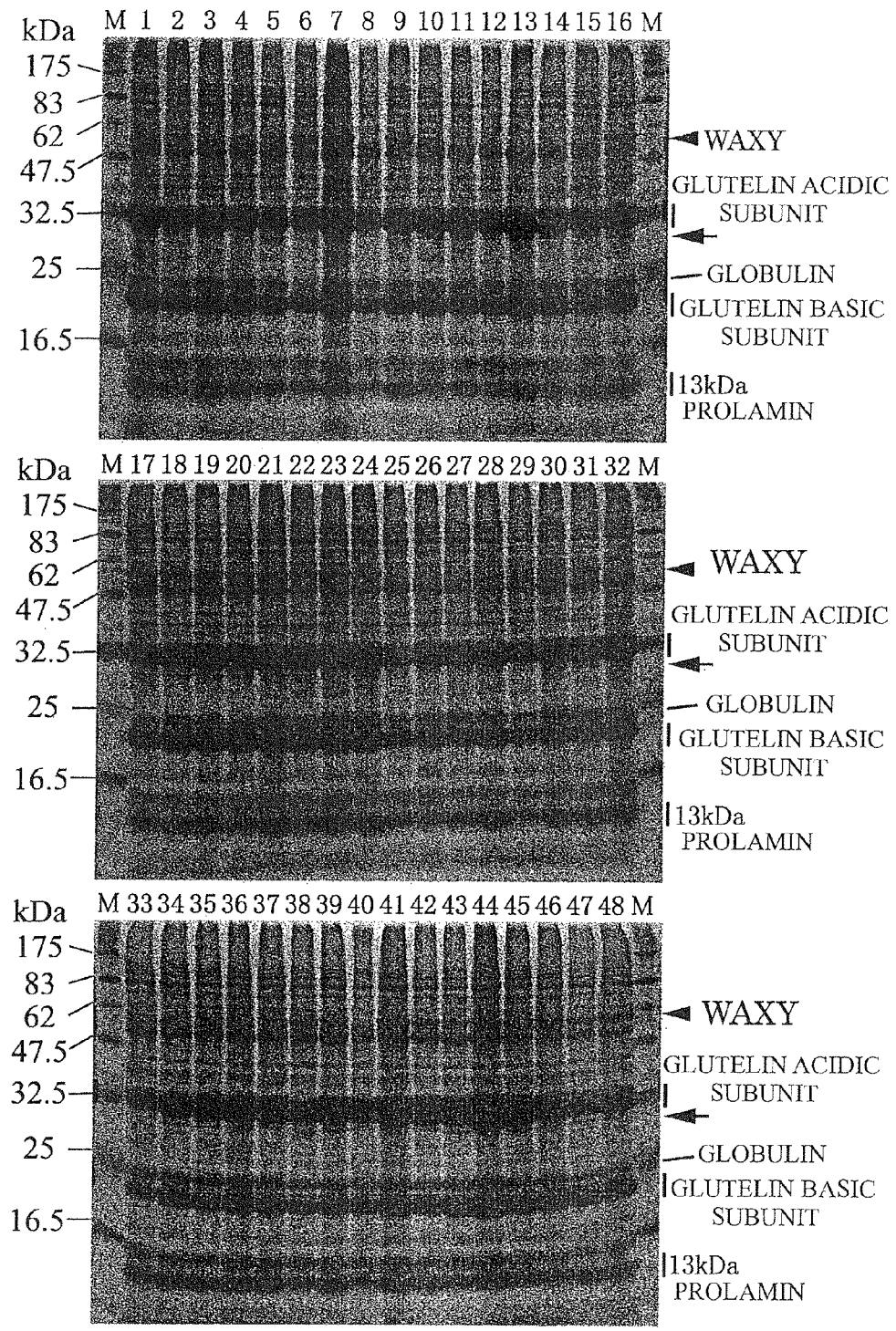
FIG. 1 shows photographs indicating the composition of the seed proteins of 48 rice accessions. Detection was carried out by SDS-PAGE followed by CBB staining. The numbers at the top of the lanes correspond to the numbers in Table 1. The numbers on the left indicate molecular weight. Glutelin acidic subunits, glutelin basic subunits, globulin, and 13 kDa prolamin are indicated on the right. The bands near 60 kDa (WAXY) and 28 kDa (GluD-1) which showed polymorphism are indicated by an arrow head and an arrow, respectively.

The present invention provides DNAs encoding the rice glutelin GluD-1 protein. More specifically, as a preferred embodiment of the present invention, for example, a DNA of any one of (a) to (d) below is provided:
(a) a DNA comprising the nucleotide sequence of SEQ ID NO: 1;
(b) a DNA encoding the amino acid sequence of SEQ ID NO: 2;
(c) a DNA encoding a protein comprising an amino acid sequence with one or more amino acid substitutions, deletions, additions, and/or insertions in the amino acid sequence of SEQ ID NO: 2, wherein the protein is functionally equivalent to a protein comprising the amino acid sequence of SEQ ID NO: 2; and
(d) a DNA that hybridizes under stringent conditions with a DNA comprising the nucleotide sequence of SEQ ID NO: 1, and encodes a protein functionally equivalent to a protein comprising the amino acid sequence of SEQ ID NO: 2.

The nucleotide sequence of the rice glutelin gene GluD-1 of the present invention is shown in SEQ ID NO: 1, and the amino acid sequence encoded by this nucleotide sequence is shown in SEQ ID NO: 2.

DNAs encoding the GluD-1 protein of the present invention include DNAs in the form of genomic DNA, cDNA synthesized from mRNA, chemically synthesized DNA, and such.

In the present invention, proteins encoded by the DNAs of the present invention of any one of the above-mentioned (a) to (d) may be described as "proteins of the present invention".

Proteins of the present invention are also included in the present invention.

The term "protein" in the present invention refers to a polymer comprising a plurality of amino acids, and the amino-acid length is not particularly limited. Therefore, proteins of the present invention also include the so-called "polypeptides" and "oligopeptides". Proteins of the present invention also include both unmodified and modified proteins in their naturally occurring form. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, γ-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA-mediated addition of amino acids to proteins such as arginylation, and ubiquitination.

Polypeptides of the present invention can be produced by general chemical synthesis methods according to their amino acid sequences, and such methods include peptide synthesis methods by normal liquid phase methods and solid phase methods. Such peptide synthesis methods more specifically include the stepwise elongation method in which each amino acid is successively synthesized one by one based on the amino acid sequence information to lengthen the chain, and the fragment condensation method in which fragments comprising a few amino acids are synthesized in advance and then each of these fragments are subjected to coupling reactions. Either method can be used for the synthesis of the proteins of the present invention.

Condensation methods used in such peptide synthesis methods can be carried out according to various types of methods. Specific examples include the azide method, mixed acid anhydride method, DCC method, active ester method, oxidation-reduction method, diphenylphosphoryl azide (DPPA) method, and Woodward method.

Generally used solvents can be suitably used as the solvents that can be utilized for these various methods. Such examples include dimethylformamide (DMF), dimethylsulfoxide (DMSO), hexaphosphoroamide, dioxane, tetrahydrofuran (THF), ethyl acetate, and mixed solvents thereof. During the above-mentioned peptide synthesis reaction, amino acids and peptide carboxyl groups that are not involved in the reaction can generally be protected as lower alkyl esters such as methyl ester, ethyl ester, or tertiary butyl ester, or as benzyl ester, p-methoxybenzyl ester, p-nitrobenzyl ester aralkyl ester, or such by esterification. Furthermore, amino acids carrying a functional group on their side chain, for example, the hydroxyl group on Tyr may be protected by an acetyl group, a benzyl group, a benzyloxycarbonyl group, a tertiary butyl group, or such but such protection is not necessarily essential. Furthermore, for example, the guanidino group of Arg can be protected by a suitable protecting group such as nitro group, tosyl group, 2-methoxybenzenesulfonyl group, mesitylene-2-sulfonyl group, benzyloxycarbonyl group, isobornyloxycarbonyl group, or adamantyloxycarbonyl group.

The proteins of the present invention obtainable as described above can be appropriately purified according to normal methods generally used in the area of peptide chemistry such as ion exchange resin, partition chromatography, gel chromatography, affinity chromatography, high performance liquid chromatography (HPLC), and countercurrent distribution method.

Proteins of the present invention can be obtained, for example, from proteins comprising the amino acid sequence of SEQ ID NO: 2 or by genetic engineering techniques in which the DNA of SEQ ID NO:1 is synthesized, then introduced into a suitable vector, and then expressed in host cells.

Proteins of the present invention can be prepared as a recombinant polypeptide or a naturally occurring polypeptide by methods known to those skilled in the art. Recombinant polypeptides can be prepared, for example, by incorporating a DNA encoding a protein of the present invention (for example, a DNA comprising the nucleotide sequence of SEQ ID NO: 1) into a suitable vector, collecting transformants obtained by introducing this vector into suitable host cells, and after obtaining an extract thereof, purifying it by chromatography such as ion exchange, reverse phase, or gel filtration, or by affinity chromatography in which antibodies against the protein of the present invention are immobilized onto the column, or by combining a plurality of such columns.

When proteins of the present invention are expressed as fusion polypeptides with a glutathione S-transferase protein, or as recombinant polypeptides with multiple additions of histidines in host cells (for example, a plant cell or a microbial cell), the expressed recombinant polypeptides can be purified using a glutathione column or a nickel column. After the fused polypeptide is purified, regions other than the polypeptide of interest can be removed from the fused polypeptide, as necessary, by cleavage with thrombin, factor Xa, or such.

Naturally derived proteins can be isolated by methods well known to those skilled in the art, for example, by purifying extracts of tissues or cells expressing the proteins of the present invention by subjecting them to an affinity column to which antibodies having affinity to the proteins of the present invention are bound. The antibodies may be polyclonal antibodies or monoclonal antibodies.

Proteins of the present invention can be utilized, for example, in the production of antibodies that recognize the proteins of the present invention and such.

DNAs encoding the proteins of the present invention can be prepared by methods known to those skilled in the art. For example, they can be prepared by producing a cDNA library from cells expressing the proteins of the present invention, then performing hybridization using a portion of the DNA encoding a protein of the present invention (for example, the nucleotide sequence of SEQ ID NO: 1) as probe. The cDNA library may be prepared, for example, by a method described in the literature (Sambrook, J. et al., Molecular Cloning, Cold Spring Harbor Laboratory Press (1989)), or a commercially available DNA library may be used. Alternatively, DNAs can be produced by preparing RNAs from cells expressing a protein of the present invention, synthesizing cDNAs using reverse transcriptase, and then synthesizing oligoDNAs based on the DNAs encoding the proteins of the present invention (for example, the nucleotide sequence of SEQ ID NO: 1), and performing PCR reactions using them as primers to amplify the cDNAs encoding the proteins of the present invention.

By determining the nucleotide sequence of the obtained cDNA, the translation region encoded by the cDNA can be determined, and the amino acid sequence of the protein of the present invention can be obtained. Furthermore, the obtained cDNA can also be used as a probe for screening a genomic DNA library to isolate genomic DNA.

Specifically, the following processes may be carried out. First, mRNAs are isolated from cells, tissues, and organs expressing the protein of the present invention. mRNAs are isolated by known methods, for example, by preparing total RNAs using guanidine ultracentrifugation methods (Chirgwin, J. M. et al., Biochemistry (1979) 18, 5294-5299), AGPC methods (Chomczynski, P. and Sacchi, N., Anal. Biochem. (1987) 162, 156-159), or such, and then purifying mRNAs from the total RNAs using an mRNA Purification Kit (Pharmacia) or such. The mRNAs can also be prepared directly by using a QuickPrep mRNA Purification Kit (Pharmacia).

cDNAs are synthesized from the obtained mRNAs using reverse transcriptase. cDNAs may be synthesized using the AMV Reverse Transcriptase First-strand cDNA Synthesis Kit (Seikagaku Corporation) and such. Alternatively, by using the primers and such described in the present invention, cDNAs may be synthesized and amplified following the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) that uses the 5'-Ampli FINDER RACE Kit (manufactured by Clontech), and polymerase chain reaction (PCR). A desired DNA fragment is prepared from the obtained PCR products and linked to a vector DNA. A recombinant vector is produced from this and introduced into *E. coli* and such, and a desired recombinant vector is prepared from a selected colony. The nucleotide sequence of the desired DNA may then be identified through known methods such as the dideoxynucleotide chain termination method.

Furthermore, when producing DNAs encoding the proteins of the present invention, the DNAs may be designed to have nucleotide sequences that are expressed more efficiently by considering the codon usage frequency in the host used for expression (Grantham R. et al., Nucleic Acids Research (1981) 9, 43-74). DNAs encoding the proteins of the present invention can be modified by commercially available kits or known methods. Examples of the modification include digestion with restriction enzymes, insertion of a synthetic oligonucleotide or a suitable DNA fragment, addition of a linker, and insertion of the initiation codon (ATG) and/or a stop codon (TAA, TGA, or TAG).

DNAs encoding the proteins of the present invention include a DNA encoding a protein comprising an amino acid sequence with one or more amino acid substitutions, deletions, additions, and/or insertions in the amino acid sequence of SEQ ID NO: 2, wherein the protein is functionally equivalent to a protein comprising the amino acid sequence of SEQ ID NO: 2.

Herein, the phrase "functionally equivalent to a protein comprising the amino acid sequence of SEQ ID NO: 2" means that the target protein has biological function or activity or biochemical function or activity similar or equivalent to a protein of the present invention. Such function includes, for example, the function of expressing specifically in a seed of a plant, such as the function of expressing specifically in an albumen tissue of a plant. Preferably such function is the function of expressing specifically in an endosperm of a plant.

In the present invention, "expressing specifically in an albumen tissue" means that compared to the expression level in tissues other than an albumen tissue, the amount of expression is at least 1,000 times or more in an albumen tissue, and the largest promoter activity in tissues other than an albumen tissue is less than 0.05 pmoles/µg protein/min. Furthermore, in the present invention, "expressing specifically in an endosperm" means that the endosperm alone becomes colored with X-Gluc when the β-glucuronidase gene is expressed under the control of the GluD-1 promoter.

Therefore, assessment of whether or not a target protein has biological properties equivalent to those of a protein of the present invention can be evaluated by methods well known to those skilled in the art. The most common method is to cultivate a plant that has been introduced with a DNA encoding a protein of this invention, and determining whether or not there is seed-specific expression (for example, expression specific to plant albumen tissues, preferably expression specific to an endosperm of a plant).

Whether or not a test gene encodes a protein expressed specifically in a seed of a plant can be evaluated, for example, by extracting mRNAs from each tissue of the plant, and performing Northern blot analysis using oligonucleotide probes that hybridize to the test gene.

Whether or not a test gene has the above-mentioned function can be evaluated by suppressing the expression of a test gene in a plant using an antisense technique or such, and analyzing the phenotype of that plant.

Methods for preparing a protein functionally equivalent to a certain protein that are well known to those skilled in the art include methods for introducing mutations into the amino acid sequence of a protein. Specifically, one skilled in the art can prepare a protein functionally equivalent to a protein comprising the amino acid sequence of SEQ ID NO: 2 by introducing appropriate mutations into this amino acid sequence using site-directed mutagenesis (Hashimoto-Gotoh, T. et al., Gene (1995) 152, 271-275; Zoller, M J, and Smith, M., Methods Enzymol. (1983) 100, 468-500; Kramer, W. et al., Nucleic Acids Res. (1984) 12, 9441-9456; Kramer W, and Fritz H J, Methods. Enzymol. (1987) 154, 350-367; Kunkel, T A, Proc. Natl. Acad. Sci. USA. (1985) 82, 488-492; Kunkel, Methods Enzymol. (1988) 85, 2763-2766) and the like. Amino acid mutations in a protein may also occur naturally. Furthermore, mutation of the amino acid sequence of the encoded protein due to mutations in the nucleotide sequence may also occur in nature. For example, as long as a protein of the present invention is encoded, DNAs comprising any nucleotide sequence based on genetic code degeneracy may also be included in the DNAs of the present invention.

Regardless of whether they are artificial or naturally occurring, proteins functionally equivalent to the proteins of the present invention, which comprise an amino acid sequence in which one or more amino acid sequences are mutated in the amino acid sequence of SEQ ID NO: 2 identified by the present inventors, are included in the proteins (polypeptides) of the present invention. Furthermore, DNAs encoding the proteins of the present invention include, for example, mutants, derivatives, alleles, variants, and homologs encoding a protein comprising an amino acid sequence with one or more amino acid substitutions, deletions, additions, and/or insertions in the amino acid sequence of SEQ ID NO: 2.

The number of mutated amino acids in the above-mentioned mutant is not particularly limited as long as the functions of the proteins of the present invention are maintained, but may ordinarily be 15 amino acids or less, preferably ten amino acids or less, more preferably five amino acids or less, and even more preferably one to four amino acids.

The amino acid residues to be mutated are preferably mutated to other amino acids that conserve the properties of the amino acid side chain. Examples of amino acid side chain properties are: hydrophobic amino acids (A, I, L, M, F, P, W, Y, and V), hydrophilic amino acids (R, D, N, C, E, Q, G, H, K, S, and T), and amino acids comprising the following side chains: aliphatic side chains A, V, L, I, and P); hydroxyl-containing side chains (S, T, and Y); sulfur-containing side chains (C and M); carboxylic acid- and amide-containing side chains (D, N, E, and Q); basic side chains (R, K, and H); and aromatic ring-containing side chains (H, F, Y, and W) (all amino acids are represented by one-letter codes in parentheses).

A protein comprising a modified amino acid sequence, in which one or more amino acid residues are deleted, added, and/or replaced with other amino acids in a certain amino acid sequence, is known to retain its original biological function (activity) (Mark, D. F. et al., Proc. Natl. Acad. Sci. USA (1984) 81, 5662-5666; Zoller, M. J. & Smith, M., Nucleic Acids Research (1982) 10, 6487-6500; Wang, A. et al., Science 224, 1431-1433; Dalbadie-McFarland, G et al., Proc. Natl. Acad. Sci. USA (1982) 79, 6409-6413).

When a specific amino acid sequence (for example SEQ ID NO: 2) is disclosed, those skilled in the art can appropriately produce a protein comprising the amino acid-modified sequence based on this amino acid sequence, and evaluate whether or not the protein has the above-mentioned function to appropriately select a protein (polypeptide) of the present invention.

Proteins in which several amino acid residues have been added to an amino acid sequence of a protein of the present invention include fusion proteins containing this protein. Fusion proteins are proteins in which such a protein and another protein (peptide or polypeptide) are fused with each other. A fusion protein can be prepared by ligating a DNA (for example SEQ ID NO: 1) encoding a protein of the present invention (for example SEQ ID NO: 2) and a DNA encoding another protein (peptide or polypeptide) such that the frames match, inserting this sequence into an expression vector, and expressing it in a host. Techniques known to those skilled in the art can be used for this purpose. The other protein (peptide or polypeptide) subjected to fusion with a protein of the present invention is not particularly limited.

Examples of other proteins to be fused to the proteins of the present invention include, GST (glutathione-S-transferase), immunoglobulin constant region, β-galactosidase, MBP (maltose-binding protein), and such. Commercially available DNAs encoding these proteins (peptides or polypeptides) can be fused with DNAs encoding the proteins of the present invention. A fusion protein can be prepared by expressing the prepared fusion protein.

Methods that use hybridization techniques are well known to those skilled in the art as examples of other methods for preparing proteins that are functionally equivalent to a certain protein (Sambrook, J. et al., Molecular Cloning 2nd ed., 9.47-9.58, Cold Spring Harbor Lab. press, 1989). More specifically, based on the DNA (the nucleotide sequence of SEQ ID NO: 1) encoding a protein of the present invention or a part thereof, those skilled in the art can generally isolate DNAs highly homologous to this from a DNA sample derived from homologous or heterologous plants to isolate proteins functionally equivalent to proteins of the present invention from the DNAs.

The present invention includes proteins encoded by a DNA that hybridizes with the DNA encoding a protein of the present invention, and are functionally equivalent to a protein of the present invention. Such proteins include homologs of rice or other plants (for example, proteins derived from plants such as maize, wheat, and barley).

Those skilled in the art can appropriately select hybridization conditions for isolating DNAs encoding proteins functionally equivalent to proteins of the present invention. The hybridization conditions are, for example, low stringency conditions. "Low stringency conditions" refers to washing after hybridization under conditions such as 42° C., 0.1×SSC, 0.1% SDS, or preferably 50° C., 0.1×SSC, 0.1% SDS. More preferable hybridization conditions include high stringency conditions. High stringency conditions are, for example, conditions of 65° C., 5×SSC, and 0.1% SDS. Under these conditions, increasing the temperature is expected to lead to efficient yield of DNAs with higher homology. However, multiple factors such as temperature and salt concentration are considered to be factors affecting the hybridization stringency, and those skilled in the art can achieve similar stringencies by appropriately selecting these factors.

In place of hybridization, a gene amplification technique (PCR) (Current protocols in Molecular Biology edit. Ausubel et al., (1987) Publish. John Wiley & Sons Section 6.1-6.4) can be utilized to isolate a DNA fragment highly homologous to a DNA encoding a protein of the present invention by using a primer which is designed based on a portion of the DNA (for example, SEQ ID NO: 1) encoding a protein of the present invention, and a protein functionally equivalent to proteins of the present invention can be obtained based on such DNA.

The proteins of the present invention may be in the form of a "mature" polypeptide, or may be a part of a larger polypeptide such as a fusion polypeptide. The proteins of the present invention may include leader sequences, pro-sequences, sequences which are useful in purification such as multiple histidine residues, or additional sequences for securing stability during recombinant production.

Proteins functionally equivalent to proteins of the present invention, which are encoded by DNAs isolated by these hybridization techniques and gene amplification techniques, generally have high amino acid sequence homology with proteins of the present invention (for example, SEQ ID NO: 2). High homology usually refers to a sequence identity at the amino acid level of at least 50% or higher, preferably 75% or higher, more preferably 85% or higher, and even more preferably 95% or higher (for example, 96% or higher, 97% or higher, 98% or higher, or 99% or higher). Protein homology can be determined by following the algorithm described in literature (Wilbur, W. J. and Lipman, D. J., Proc. Natl. Acad. Sci. USA (1983) 80, 726-730).

The amino acid sequence identity can be determined, for example, by the BLAST algorithm of Karlin and Altschul (Proc. Natl. Acad. Sci. USA (1990) 87, 2264-2268; Proc. Natl. Acad. Sci. USA (1993) 90, 5873-5877). A program called BLASTX has been developed based on this algorithm (Altschul et al., J. Mol. Biol. (1990) 215, 403-410). When amino acid sequences are analyzed by BLASTX, parameters are set, for example, at score=50 and wordlength=3. When using the BLAST and Gapped BLAST programs, the default parameters of each program are used. Specific procedures for these analytical methods are known (http://www.ncbi.nlm.nih.gov).

The present invention provides DNAs for suppressing the expression of DNAs encoding the proteins of the present invention. In the present invention, the phrase "suppressing the expression of DNAs" includes suppression of DNA transcription and suppression of translation into proteins. Furthermore, it includes not only a complete cessation of DNA expression but also decreased expression.

As a method for suppressing the expression of certain endogenous genes in plants, methods that utilize antisense techniques are often used by those skilled in the art. There are multiple factors such as those below which are involved in actions that cause antisense RNA-encoding DNAs to suppress the target gene expression. These factors include: inhibition of transcription initiation by triple strand formation; suppression of transcription by hybrid formation at the site where the RNA polymerase forms a local open loop structure; transcription inhibition by hybrid formation with the RNA being synthesized; suppression of splicing by hybrid formation at the junction between an intron and an exon; suppression of splicing by hybrid formation at the site of spliceosome formation; suppression of translocation from the nucleus to the cytoplasm by hybrid formation with mRNA; suppression of splicing by hybrid formation at the capping site or the poly A addition site; suppression of translation initiation by hybrid formation at the binding site for translation initiation factors; suppression of translation by hybrid formation at the site of ribosome binding near the initiation codon; inhibition of peptide chain elongation by hybrid formation in the translated region or at the polysome binding site of mRNA; and suppression of gene expression by hybrid formation at the site of interaction between nucleic acids and proteins. These factors suppress the target gene expression by inhibiting the process of transcription, splicing, or translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)," Nihon Seikagakukai Hen (ed. The Japanese Biochemical Society), Tokyo Kagaku Dozin, pp. 319-347, 1993).

A DNA encoding an antisense RNA of the present invention may suppress the expression of the GluD-1 gene, which is the target gene, by any of the above actions. In one embodiment, it is believed that an antisense sequence designed to be complementary to the untranslated region near the 5' end of a gene's mRNA can effectively inhibit translation of the gene. It is also possible to use sequences complementary to the coding region or the untranslated region on the 3' side. The antisense RNA-encoding DNA used in the present invention also includes not only DNAs having an antisense sequence against sequence of the translated region but also those that have an antisense sequence against sequence of the untranslated region of the gene. The antisense RNA-encoding DNA to be used is connected downstream of a suitable promoter, and preferably, a sequence containing the transcription termination signal is connected on the 3' side. The sequence of the DNA encoding an antisense RNA is preferably a sequence complementary to the target gene or a part thereof, and it does not need to be perfectly complementary, as long as it can effectively inhibit the gene expression. The transcribed RNA has preferably 90% or higher, and most preferably 95% or higher complementarity to the transcripts of the target gene.

The DNA encoding an antisense RNA of the present invention can be prepared, for example, by the phosphorothioate method (Stein, 1988 Physicochemical properties of phosphorothioate oligodeoxynucleotides. Nucleic Acids Res. (1988) 16, 3209-21) based on the sequence information of the DNA encoding a protein of the present invention (for example, SEQ ID NO: 1).

DNA encoding an RNA having ribozyme activity can also be used to inhibit the expression of genes. A ribozyme refers to an RNA molecule that has catalytic activity. Ribozymes can have a variety of activities. Research on ribozymes as RNA cleaving enzymes has enabled the design of a ribozyme that site-specifically cleaves RNA. While ribozymes such as the group I intron type or the M1RNA contained in RNaseP have a size of 400 nucleotides or more, others have an activity domain of about 40 nucleotides which are called the hammerhead type or hairpin type (Makoto Koizumi and Eiko Ohtsuka (1990) Tanpakushitsu Kakusan Kohso (Protein, Nucleic acid, and Enzyme) 35, 2191).

For example, the self-cleavage domain of a hammerhead type ribozyme cleaves at the 3' side of C15 of G13U14C15. Formation of a nucleotide pair between U14 and A at the ninth position is considered important for the activity. Furthermore, it has been shown that the cleavage also occurs when the nucleotide at the 15th position is A or U instead of C (M. Koizumi et al., FEBS Lett. (1988) 228, 225). If the substrate binding site of the ribozyme is designed to be complementary to the RNA sequence adjacent to the target site, one can create a restriction-enzyme-like RNA cleaving ribozyme which recognizes the sequence UC, UU, or UA within the target RNA (M. Koizumi et al., FEBS Lett. (1988) 239, 285; Makoto Koizumi and Eiko Ohtsuka (1990) Tanpakushitsu Kakusan Kohso (Protein, Nucleic acid and Enzyme), 35: 2191; M. Koizumi et al., Nucleic Acids Res. (1989) 17, 7059).

The hairpin-type ribozyme is also useful for the objective of the present invention. A hairpin-type ribozyme can be found, for example, in the minus strand of the satellite RNA of the tobacco ringspot virus (J. M. Buzayan, Nature (1986) 323, 349). It has been shown that this ribozyme can also be designed to cleave RNA in a target-specific manner (Y. Kikuchi and N. Sasaki Nucleic Acids Res. (1992) 19, 6751; Yo Kikuchi (1992) Kagaku To Seibutsu (Chemistry and Biology) 30, 112).

When using a DNA that suppresses the expression of a DNA encoding a protein of the present invention for transformation, one may consider administration to a target plant by ex vivo or in vivo methods using, for example, viral vectors such as retroviral vector, adenovirus vector, or adeno-associated virus vector, or non-viral vectors such as liposomes.

Inhibition of gene expression can also be carried out by RNA interference (RNAi) using double-stranded RNA having a sequence identical or similar to a target gene sequence. RNAi refers to a phenomenon that when double-stranded RNA having a sequence identical or similar to a target gene sequence is introduced into a cell, the expression of both the introduced exogenous gene and the target endogenous gene is inhibited. It is thought that in RNAi, the initially introduced double-stranded RNA is degraded into small fragments, these fragments become indicators of a target gene in some form, and as a result the target gene is degraded. The RNA used for RNAi does not necessarily have to be completely identical to the DNA encoding a protein of the present invention or to a partial region of the DNA, although preferably it is completely homologous. A DNA molecule that may synthesize a double-stranded RNA in a cell may also be introduced.

In the present invention, the sequence of a DNA encoding an antisense RNA against a GluD-1 gene or a DNA encoding an RNA with inhibitory activity as a result of RNAi effect can be suitably designed by those skilled in the art based on the DNA sequence of a GluD-1 gene shown in the Sequence Listing of the present specification.

Endogenous gene expression can also be suppressed by co-suppression through transformation with DNA having a sequence identical or similar to the target gene sequence. "Co-suppression" refers to a phenomenon that when a gene having a sequence identical or similar to the target endogenous gene is introduced into plants by transformation, expression of both the introduced exogenous gene and the target endogenous gene is suppressed. Although the detailed mechanism of co-suppression is unknown, it is frequently observed in plants (Curt Biol. 7: R793, 1997, Curr. Biol. (1996) 6, 810). For example, if one wishes to obtain a plant in which the GluD-1 gene is co-suppressed, the plant of interest can be transformed with a vector DNA constructed so as to express the GluD-1 gene or a DNA having similar sequence, and a plant having the characteristics of a GluD-1 mutant can be selected from the obtained plants. The gene to be used for co-suppression does not have to be completely identical to the target gene, but it should have at least 70% or more, preferably 80% or more, and more preferably 90% or more (e.g. 95% or more) sequence identity. Sequence identity may be determined using the above-described search.

In addition, endogenous gene expression in the present invention can also be suppressed by transforming the plant with a gene having a dominant negative phenotype of the target gene. Herein, "DNA encoding a protein having a dominant negative phenotype" refers to a DNA encoding a protein which when expressed, has the function of eliminating or reducing the activity of the protein encoded by an endogenous gene of the present invention inherent to the plant. Whether or not the DNA of interest has the function of eliminating or reducing the activity of an endogenous gene of the present invention can be determined as described above by determining if the DNA of interest is expressed specifically in the seed of the plant, for example, whether or not it is expressed specifically in an albumen tissue, or preferably whether or not it is expressed specifically in the endosperm.

Furthermore, the present invention provides DNAs having promoter activity. Examples of such DNAs include genomic DNAs in the upstream region of a DNA encoding a protein of the present invention, such as DNAs comprising the nucleotide sequence of SEQ ID NO: 3.

In the present invention, the above-mentioned DNAs having promoter activity may be referred to as "promoter DNAs".

Promoter DNAs of the present invention also include DNAs highly homologous to a DNA comprising the nucleotide sequence of SEQ ID NO: 3, as long as they have promoter activity. Such DNA is, for example, a DNA comprising a nucleotide sequence with one or more nucleotide deletions, substitutions, additions, and/or insertions to the nucleotide sequence of SEQ ID NO: 3, and which is functionally equivalent to a DNA comprising the nucleotide sequence of SEQ ID NO: 3.

Herein, "functionally equivalent to a DNA comprising the nucleotide sequence of SEQ ID NO: 3" means that the target DNA has promoter activity similar to that of a promoter DNA of the present invention. Methods well known to those skilled in the art for preparing a DNA highly homologous to a DNA comprising the nucleotide sequence of SEQ ID NO: 3 are, for example, methods for introducing mutations into a DNA comprising the nucleotide sequence of SEQ ID NO: 3 using site-directed mutagenesis methods and such.

Furthermore, DNAs having high homology to a DNA comprising the nucleotide sequence of SEQ ID NO: 3 can be obtained by common hybridization techniques and PCR techniques. For example, a DNA having high homology to a DNA comprising the nucleotide sequence of SEQ ID NO: 3 can be isolated from rice or other plants using a DNA comprising the nucleotide sequence of SEQ ID NO: 3 or a part thereof as a probe and oligonucleotides that hybridize specifically to a DNA comprising the nucleotide sequence of SEQ ID NO: 3 as primers. For isolation of such DNAs, hybridization reaction is carried out preferably under stringent conditions. For the hybridization, conditions similar to those for the above-mentioned albumen tissue-specific DNA can be used. High homology refers to sequence identity of preferably 50% or higher, more preferably 70% or higher, and most preferably 90% or higher (for example, 95%, 96%, 97%, 98%, or 99% or higher) to the whole nucleotide sequence of SEQ ID NO: 3.

The nucleotide sequence identity can be determined by the BLAST algorithm of Karlin and Altschul (Proc. Natl. Acad. Sci. USA (1990) 87, 2264-2268; Proc. Natl. Acad. Sci. USA (1993) 90, 5873-5877). A program called BLASTN has been developed based on this algorithm (Altschul et al., J. Mol. Biol. (1990) 215, 403-410). When nucleotide sequences are analyzed by BLASTN, parameters are set, for example, at score=100 and wordlength=12. When using the BLAST and Gapped BLAST programs, the default parameters of each program are used. Specific procedures for these analytical methods are known (http://www.ncbi.nlm.nih.gov).

Furthermore, if a DNA having high homology to a DNA encoding a protein of the present invention is obtained, the activity of the obtained DNA is confirmed, and then a genomic DNA upstream of this DNA is obtained, this genomic DNA is considered to have promoter activity. DNAs having promoter activity of the present invention can be obtained this way using DNAs encoding the proteins of the present invention.

More specifically, preferred embodiments of the DNAs having promoter activity of the present invention are the DNAs of any one of the following:
(a) a DNA comprising the nucleotide sequence of SEQ ID NO: 3;
(b) a DNA comprising a nucleotide sequence with one or more nucleotide deletions, substitutions, additions, and/or insertions in the nucleotide sequence of SEQ ID NO: 3, and which is functionally equivalent to the DNA comprising the nucleotide sequence of SEQ ID NO: 3; and
(c) a DNA that hybridizes under stringent conditions with a DNA comprising the nucleotide sequence of SEQ ID NO: 3.

DNAs having promoter activity of the present invention are DNAs characterized with a promoter activity specific to albumen tissues, in particular, the endosperm of a plant. Furthermore, the phrase "promoter activity specific to endosperm" in the present invention means that the maximum promoter activity in tissues other than the endosperm is less than 0.05 pmoles/µg protein/min. In the present invention, the phrase "expressed specifically in the endosperm" means that the endosperm alone becomes colored with X-Gluc when the β-glucuronidase gene is expressed under the control of the GluD-1 promoter. The period in which DNAs having promoter activity of the present invention show endosperm-specific expression is preferably the early stage of seed maturation. For example, in rice, this early stage of seed maturation refers to the period of 7 to 15 days after flowering, but it goes without saying that the period differs depending on the type of plant.

The origin of a promoter DNA of the present invention is not limited as long as the promoter DNA has promoter activity.

Whether or not DNAs prepared as described above have promoter activity can be detected by well known reporter assays and such using reporter genes. The reporter genes are not particularly limited as long as their expression is detectable, and include the CAT gene, lacZ gene, luciferase gene, β-glucuronidase (GUS) gene, and GFP gene, which are generally used by those skilled in the art.

The expression level of the reporter genes can be measured by methods known to those skilled in the art according to the type of reporter. For example, the expression level of the reporter gene can be measured by detecting acetylation of chloramphenicol by the gene product when the reporter gene is the CAT gene.

The expression level of the reporter gene can be measured by detecting color development of a colored compound as a result of the catalytic action of the gene product when the reporter gene is the lacZ gene.

The expression level of the reporter gene can be measured by detecting fluorescence of a fluorescent compound as a result of the catalytic action of the gene product when the reporter gene is the luciferase gene.

The expression level of the reporter gene can be measured by detecting luminescence of Glucuron (ICN) or color development of 5-bromo-4-chloro-3-indolyl-beta-glucuronide (X-Gluc) as a result of the catalytic action of the gene product when the reporter gene is the GUS gene.

The expression level of the reporter gene can be measured by detecting fluorescence of the GFP protein when the reporter gene is the GFP gene.

A promoter DNA of the present invention can be used to express an exogenous gene specifically in endosperm. Herein, an "exogenous gene" means any exogenous DNA that can induce transcription by a promoter DNA of the present invention. Therefore, in addition to protein-encoding DNAs, an exogenous gene includes RNA-encoding DNAs (for example, the above-mentioned antisense RNA-encoding DNA, DNA with ribozyme activity, DNA encoding RNA having an activity of inhibiting DNA expression by RNAi effect, DNA encoding an RNA that suppresses DNA expression by co-suppression effect, and such).

To express an exogenous gene specifically in the endosperm using a promoter DNA of the present invention, for example, a vector containing a promoter DNA of the present invention is produced, and an exogenous gene is operably linked downstream of the promoter DNA of the present invention in this vector.

That is, promoter DNAs of the present invention include DNAs having a structure in which an exogenous gene is operably linked downstream of a promoter DNA.

The phrase "operably linked" means that an exogenous gene and a promoter DNA of the present invention are linked in a manner that allows the exogenous gene to be expressed in response to activation of the promoter DNA of the present invention. Since the promoter DNA of the present invention has high endosperm-specific activity, a gene whose expression in the endosperm is particularly preferred as an exogenous gene, and for example, a gene used for production of useful substances such as functional components or vaccines, 7Crp gene, and novokinin gene can be used favorably.

In addition, for example, the number of the aleurone layers and the subaleurone layers which accumulate a lot of proteins is determined by intercellular interactions. Since the endosperm is in contact with the subaleurone layer, interaction with the endosperm is considered to be important. The number of aleurone and subaleurone layers may also be regulated by identifying such interaction factors, and expressing them specifically in the endosperm as exogenous genes using a promoter DNA of the present invention.

In the present invention, the above-mentioned DNAs encoding a protein of the present invention, DNAs for suppressing expression of a DNA encoding a protein of the present invention, and promoter DNAs are collectively described as "DNAs of the present invention" in some cases.

Furthermore, the present invention provides vectors comprising the above-mentioned DNAs of the present invention.

In addition to the above-mentioned vectors used for recombinant protein production, vectors of the present invention include vectors for expressing DNAs of the present invention in plant cells for the production of transformed plants. Such vectors preferably include a promoter sequence that can be transcribed in plant cells, and a terminator sequence comprising a polyadenylation site necessary for stabilization of transcription products. Promoter DNA of the present invention can be used for the promoter sequence, or other promoter sequences can also be used.

A vector used for transformation of a plant cell is not particularly limited as long as it can express an inserted exogenous gene in the cell. For example, a vector having a promoter that constantly expresses genes in plant cells (for example, the 35S promoter of the cauliflower mosaic virus), and a vector having a promoter that is inductively activated by an external stimulus may be used. The above-mentioned "plant cells" include plant cells of various morphologies, for example, suspension culture cells, protoplasts, sections of leaves, and calli.

A vector of the present invention may contain a promoter that constantly or inducibly expresses a protein of the present invention. A promoter for constant expression may be, for example, the 35S promoter from cauliflower mosaic virus, the actin promoter from rice, or the ubiquitin promoter from maize.

Promoters for inducible expression include, for example, promoters known to be expressible by exogenous factors including bacterial or viral infection or invasion, low temperatures, elevated temperatures, dry conditions, UV light radiation, and application of specific compounds. Examples of such promoters include the rice chitinase gene promoter and the tobacco PR protein gene promoter inducible by bacterial or viral infection or invasion; the rice "lip19" gene promoter inducible by low temperatures; the rice "hsp80" gene and "hsp72" gene promoter inducible by high temperatures; the *Arabidopsis thaliana* "rab16" gene promoter inducible by dry conditions; the parsley chalcone synthase gene promoter inducible by UV light radiation; the maize alcohol dehydrogenase gene promoter inducible by anaerobic conditions; and such. Also, the rice chitinase gene promoter and the tobacco PR protein gene promoter can be induced by specific compounds such as salicylic acid, and "rab16" can also be induced by application of phytohormone abscisic acid.

Those skilled in the art can appropriately produce vectors carrying desired DNAs using general genetic engineering techniques. Usually, various commercially available vectors can be used.

Vectors of the present invention are also useful for retaining DNAs of the present invention in host cells, and expressing proteins of the present invention.

DNAs of the present invention are generally supported in (inserted into) suitable vectors and then introduced into host cells. The vectors are not particularly limited as long as the inserted DNA is stably maintained. For example, when using *E. coli* as a host, the cloning vector is preferably a pBluescript vector (manufactured by Stratagene) and such, but various commercially available vectors may be used. Expression vectors are particularly useful when using vectors for producing the proteins of the present invention. Expression vectors are not particularly limited as long as they can express polypeptides in test tubes, *E. coil*, cultured cells, or individual plants. For example, such vectors are pBEST vector (manufactured by Promega) for expression in test tubes, pET vector (manufactured by Invitrogen) for *E. coli*, pME18S-FL3 vector (GenBank Accession No. AB009864) for cultured cells, and pME18S vector (Mol. Cell Biol. (1988) 8, 466-472) for individual organisms. Insertion of a nucleic acid of the present invention into vectors can be performed by standard methods such as ligase reactions using restriction enzyme sites.

The above-mentioned host cells are not particularly limited, and various host cells can be used depending on the purpose. Cells used for expressing the proteins of the present invention include bacterial cells (for example, *Streptococcus*, *Staphylococcus*, *E. coli*, *Streptomyces*, and *Bacillus subtilis*), insect cells (for example, *Drosophila* S2 and *Spodoptera* SF9), animal cells (for example, CHO, COS, HeLa, C127, 3T3, BHK, HEK293, Bowes melanoma cell), and plant cells. Vectors can be introduced into host cells using known methods such as the calcium phosphate precipitation method, electroporation method (Current protocols in Molecular Biology edit. Ausubel et al. (1987) Publish. John Wiley & Sons Section 9.1-9.9), lipofection (manufactured by GIBCO-BRL), and microinjection method.

To secrete host cell-expressed proteins into the lumen of endoplasmic reticulum, periplasmic space, or extracellular environment, suitable secretion signals can be incorporated into the proteins of interest. These signals may be intrinsic or exogenous to the proteins of interest.

When the proteins of the present invention are secreted into culture media, the proteins are collected by harvesting the media. When the proteins of the present invention are produced inside cells, the cells are first lysed, and then the proteins are collected.

The proteins of the present invention can be collected and purified from recombinant cell cultures by known methods including ammonium sulfate or ethanol precipitation, acidic extraction, anion or cation exchange chromatography, phosphocellulose chromatography, hydrophobic interaction chromatography, affinity chromatography, hydroxyapatite chromatography, and lectin chromatography.

Methods for expressing a DNA of the present invention in a plant include the method of incorporating a DNA of the present invention into a suitable vector and then introducing this into a living body by methods such as the electroporation method, agrobacterium method, liposome method, cationic liposome method, and such. General genetic engineering such as insertion of a DNA of the present invention into a vector can be carried out according to a conventional procedure (Molecular Cloning, 5.61-5.63). Administration into a plant may be performed by an ex vivo method or an in vivo method. A method for introducing a DNA of the present invention into a plant is preferably, for example, an Agrobacterium-mediated method for introducing a gene.

Furthermore, one can produce a transformed plant into which a DNA encoding a protein of the present invention has been introduced, and a protein of the present invention can be prepared from this plant.

Furthermore, by using recombinant proteins obtained as described above, one can prepare antibodies that bind to them. For example, one can prepare polyclonal antibodies by immunizing animals such as rabbits with purified proteins of the present invention or a partial peptide, collecting blood after a certain period of time, and removing blood clots. Further, one can prepare monoclonal antibodies by fusing antibody-producing cells of animals immunized with the above-mentioned proteins or peptides with bone tumor cells, isolating resultant single-clone cells (hybridoma) producing the antibodies of interest, and obtaining antibodies from the cells. The antibodies thus obtained can be used for purification and detection of the proteins of the present invention. The present invention includes antibodies that bind to the proteins of the present invention. Utilization of these antibodies enables detection of the location where the proteins of the present invention are expressed in plants or determination of whether or not a plant species expresses a protein of the present invention.

When producing transformed plants using the DNAs of the present invention, a DNA of the present invention is inserted into a suitable vector, the vector is introduced into a plant cell, and an obtained transformed plant cell is regenerated. The time required for this transformation is very short compared to the period of gene transfer by conventional crossing. It is also advantageous since it does not accompany other phenotypic changes.

The present invention provides transformed cells into which a vector of the present invention has been introduced. In addition to the above-mentioned cells used for producing recombinant proteins, the cells into which a vector of the present invention is introduced include plant cells used for preparing transformed plants.

There are no particular limitations on the plant cell, and examples are cells of rice, wheat, barley, maize, and such which are gramineous plants; tobacco, aubergine, bell pepper, chili pepper, and such which are solanaceous plants; persimmon and such which are Ebenaceae plants; carrot, celery, parsley, and such which are Umbelliferae plants; lily, onion, leek, and such which are Liliaceae plants; and spinach and such which are Chenopodiaceae plants.

Furthermore, the present invention includes transformed plants comprising the transformed plant cells of the present invention.

In addition to cultured cells, the plant cells of the present invention include cells within plants, and also protoplasts, shoot primordia, multiple shoots, and hairy roots. Vectors can be introduced into plant cells by using various methods known to those skilled in the art, such as polyethylene glycol methods, electroporation, *Agrobacterium*-mediated methods, and particle gun methods. Plants can be regenerated from transformed plant cells by methods known to those skilled in the art, depending on the type of plant cell. For example, for rice, methods for producing transformed plants include the method of introducing genes into protoplasts using polyethylene glycol and regenerating the plant, the method of introducing genes into protoplasts using electric pulse and regenerating the plant, the method of introducing genes directly into cells by the particle gun method and regenerating the plant, and the method of introducing genes via *Agrobacterium* and regenerating the plant. These multiple techniques have been already established and are widely used in the technical field of the invention of this application. Such methods can be suitably used in the present invention.

For efficient selection of plant cells transformed by introduction of a vector containing a DNA of the present invention, preferably the above-mentioned recombinant vector comprises a suitable selection marker gene or is introduced into the plant cell together with a plasmid vector comprising a selection marker gene. Examples of selection marker genes used for this purpose include the hygromycin phosphotransferase gene that gives resistance to the antibiotic hygromycin, neomycin phosphotransferase gene that gives resistance to kanamycin or gentamycin, and acetyl transferase gene that gives resistance to the herbicide phosphinothricin.

Plant cells introduced with a recombinant vector are placed in a known selection medium containing a suitable agent for selection according to the type of the introduced selection marker gene and the cells are cultured. This way, transformed cultured plant cells can be obtained.

Plants can be regenerated by redifferentiating transformed plant cells. Methods of redifferentiation differ depending on the type of plant cell, and examples include the method of Fujimura et al. (Plant Tissue Culture Lett. (1995) 2, 74) for rice, and the methods of Shillito et al. (Bio/Technology (1989) 7, 581) and Gorden-Kamm et al. (Plant Cell (1990) 2, 603) for maize.

Once a transformed plant in which the DNA of the present invention has been integrated into its genome is obtained, it is possible to obtain a progeny from the plant by sexual or asexual reproduction. It is also possible to obtain reproductive materials (such as seeds, fruits, spikes, tubers, tuberous roots, stubs, calli, and protoplasts) from the plant or a progeny or clone thereof, and mass-produce the plant based on such material. Thus, the present invention includes plant cells into which the DNA of the present invention has been introduced, plants containing these cells, progenies and clones of these plants, as well as reproductive materials of the plants, and their progenies and clones.

As described above, methods for producing transformed plants comprising the steps of introducing a DNA or a vector of the present invention into pant cells and regenerating a plant from the plant cells are also included in the present invention.

Furthermore, the present invention provides methods for expressing an exogenous gene specifically in the endosperm of a plant. These methods include the step of introducing a promoter DNA or a vector containing a promoter DNA of the present invention into plant cells.

Methods for producing transformed plants of the present invention also include methods in which expression of a protein of the present invention is inhibited. More specifically, expression of a protein of the present invention is inhibited by administering a DNA for suppressing the expression of a DNA encoding a protein of the present invention or a vector containing this DNA. The phrase, "expression of a protein is inhibited" in the present invention means that expression of a protein is significantly suppressed (decreased). The above-mentioned phrase "suppressing the expression" of the present invention includes transcriptional suppression of a gene encoding the protein and/or translational suppression of the gene from the transcription product.

Furthermore, the present invention also includes methods for inducing expression of an exogenous gene specifically in the endosperm of a plant and methods for inducing accumulation of an exogenous protein specifically in the endosperm of a plant, which comprise the step of expressing a DNA encoding a protein of the present invention or a vector containing this DNA in the cells of a plant. These methods enable production of plants with induced expression of an exogenous gene specifically in the endosperm of a plant or seeds thereof, or plants with induced accumulation of an exogenous protein specifically in the endosperm of a plant or seeds thereof.

The present invention provides plants produced by the above-mentioned methods of the present invention or seeds thereof.

For example, the following are included in the present invention:
(1) artificially produced plants or seeds thereof, which are plants comprising a promoter DNA or a DNA encoding a protein of the present invention, wherein expression of an exogenous gene is induced specifically in the endosperm of a plant, or seeds thereof;
(2) artificially produced plants or seeds thereof, which are plants comprising a promoter DNA or a DNA encoding a protein of the present invention, wherein accumulation of an exogenous protein is induced specifically in the endosperm of a plant, or seeds thereof; and
(3) artificially produced plants or seeds thereof, which are plants in which expression of a DNA encoding a protein of the present invention is suppressed, or seeds thereof.

Furthermore, the present invention provides agents for inducing expression of an exogenous gene specifically in the endosperm of a plant or agents for inducing accumulation of an exogenous protein specifically in the endosperm of a plant, which comprise a promoter DNA or a vector comprising such a promoter DNA of the present invention as an active ingredient.

The phrase "agents for inducing expression of an exogenous gene specifically in the endosperm of a plant" in the present invention means that agents have the effect of causing expression of an exogenous gene specifically in the endosperm of a plant, and generally refers to substances or compositions (mixtures) comprising as an active ingredient a promoter DNA or a vector containing this promoter DNA of the present invention to be used to express an exogenous gene specifically in the endosperm of a plant.

Furthermore, the phrase "agents for inducing accumulation of an exogenous protein specifically in an endosperm of a plant" in the present invention means that agents have the effect of causing accumulation of an exogenous protein specifically in the endosperm of a plant, and generally refers to substances or compositions (mixtures) comprising as an active ingredient a promoter DNA or a vector containing this promoter DNA of the present invention to be used to accumulate an exogenous protein specifically in the endosperm of a plant.

In addition to the above-mentioned promoter DNA or vector containing the promoter DNA, which is the active ingredient, the agents of the present invention may be mixed as necessary with, for example, sterilized water, physiological saline, plant oil, surfactant, lipids, solubilizing agents, buffers, preservatives, or such.

Furthermore, the present invention provides methods of screening for a candidate compound that regulates the activity of a promoter DNA of the present invention. An example is a screening method comprising the following:
(a) contacting a test compound with a cell or cell extract solution comprising a DNA having a structure in which a reporter gene is operably linked under the control of a promoter DNA of the present invention;
(b) measuring the expression level of the reporter gene; and
(c) selecting a compound that changes the expression level of the reporter gene compared to that measured in the absence of the test compound.

In the above-mentioned screening method of the present invention, a test compound is first contacted with a cell or cell extract solution comprising a DNA having a structure in which a reporter gene is operably linked under the control of a promoter DNA of the present invention.

The reporter genes used in the present screening method are not particularly limited as long as their expression is detectable, and include the CAT gene, lacZ gene, luciferase gene, and GFP gene. Examples of the "cell comprising a DNA having a structure in which a reporter gene is operably linked under the control of a promoter DNA of the present invention" include cells introduced with a vector in which such a structure has been inserted. Such vectors can be produced by methods well known to those skilled in the art. Vectors can be introduced into cells using common methods such as the calcium phosphate precipitation method, electroporation method, lipofectamine method, and microinjection method. Furthermore, cells in which this structure is inserted into the chromosome are also included. This structure can be inserted into the chromosome by methods commonly used by those skilled in the art such as gene transfer methods using homologous recombination.

The phrase "operably linked" means that a promoter DNA of the present invention and a reporter gene are linked so that expression of the reporter gene can be induced.

"A cell or cell extract solution comprising a DNA having a structure in which a reporter gene is operably linked under the control of a promoter DNA of the present invention" includes, for example, a cell extract solution included in a commercially available in vitro transcription/translation kit, into which a DNA having a structure where a promoter DNA of the present invention and a reporter gene are operably linked has been added.

"Contact" in the present screening method can be carried out by adding a test compound to the culture solution of "cells comprising a DNA having a structure in which a reporter gene is operably linked under the control of a promoter DNA of the present invention", or by adding a test compound to the above-mentioned commercially available cell extract solution containing this DNA. When the test compound is a protein, the contact can be performed, for example, by introducing a DNA vector expressing the protein into the cells.

The test compound used in the present method is not particularly limited, and includes for example, single compounds such as naturally-occurring compounds, organic compounds, inorganic compounds, proteins, or peptides, as well as compound libraries, expression products of gene libraries, cell extracts, cell culture supernatants, microbial fermentation products, marine organism extracts, or plant extracts, but are not limited thereto. The test compound may also be used with appropriate labeling when necessary. The label includes, for example, radiolabels and fluorescent labels.

In the present screening methods, the expression level of the reporter gene is then measured. The expression level of the reporter genes can be measured according to the type of reporter gene by methods known to those skilled in the art. For example, when the reporter gene is the CAT gene, the expression level of the reporter gene can be measured by detecting acetylation of chloramphenicol by the gene product. Furthermore, the expression level of the reporter gene can be measured by detecting color development of a colored compound as a result of the catalytic action of the gene expression product when the reporter gene is the lacZ gene; by detecting fluorescence of a fluorescent compound as a result of the catalytic action of the gene expression product when the reporter gene is the luciferase gene; and by detecting fluorescence of the GFP protein when the reporter gene is the GFP gene.

In the present method, the measured expression level of the reporter gene is next compared to measurement in the absence of the test compound to select compounds that cause change. The meaning of the term "change" includes both reduction and enhancement. Compounds selected in this manner are candidate compounds for regulating the promoter activity of promoter DNAs of the present invention.

Use of these candidate compounds is considered to enable more rigorous control of expression induction, and enable uniform and stable substance production in a plant factory.

Since expression of the GluD-1 gene is controlled by regulating the transcription factor RPBF, expression can be changed by controlling the expression of RPBF. The above-mentioned candidate compounds are not only used alone but may also be used in combination with this RPBF.

"Albumen tissue" in the present invention is a tissue including at least an endosperm, and may further include one or both tissues containing the aleurone layer or subaleurone layer.

"Endosperm" is a type of an albumen tissue which stores nutrients in the seeds of seed plants and provides nutrient source during embryonic development, and is a tissue derived from the inside of an embryo sac. In particular, in gramineous plants, cells around the endosperm have cambium layer-like functions and produce starch storage cells having a thin cell wall on the inner side. By the time the seeds mature, the outer cell layer becomes thick-walled and develops into an aleurone layer. When described as "endosperm" in the present invention, it refers to a region in the albumen tissue that does not substantially contain the aleurone and subaleurone layers.

This "aleurone layer" is a cell layer containing a large quantity of aleurone particles, and is formed by differentiation of cells around the albumen. The "subaleurone layer" refers to the layer between this aleurone layer and albumen.

The plants in the present invention may be albuminous seed plants, and are preferably those that accumulate seed storage proteins. There are no particular limitations on the seed storage proteins.

Specific examples of the plants include rice, wheat, barley, maize, and such which are gramineous plants; tobacco, aubergine, bell pepper, chili pepper, and such which are solanaceous plants; persimmon and such which are Ebenaceae plant; carrot, celery, parsley, and such which are Umbelliferae plants; lily, onion, leek, and such which are Liliaceae plants; and spinach and such which are Chenopodiaceae plants.

Furthermore, the present invention relates to use of a DNA or a vector of the present invention in each of the following productions:
  production of transformed plants;
  production of agents which induce expression of an exogenous gene specifically in the endosperm of a plant; and
  production of agents which induce accumulation of an exogenous protein specifically in the endosperm of a plant.

Furthermore, the present invention relates to each of the following DNAs or vectors:
  DNAs or vectors of the present invention for inducing expression of an exogenous gene specifically in the endosperm of a plant; and
  DNAs or vectors of the present invention for inducing accumulation of an exogenous protein specifically in the endosperm of a plant.

EXAMPLES

Herein below, the present invention will be specifically described with reference to the Examples, but it is not to be construed as being limited thereto.

Example 1

Identification of Novel Glutelin

Forty-eight rice accessions (Table 1) obtained from the National Institute of Agrobiological Sciences Genebank, and Nipponbare, Koshihikari, Kasalath, Nona Bokra, Koshihikari/Nona Bokra chromosome segment substitution lines (CSSLs) (Takai, T. et al., "Development of chromosome segment substitution lines derived from backcross between indica donor rice *cultivar* 'Nona bokra' and *japonica* recipient *cultivar* 'Koshihikari'", Breeding Science, (2007) 57, 257-261), Nipponbare/Kasalath backcross inbred lines (BILs) (Lin, S. Y. et al., "Mapping quantitative trait loci controlling seed dormancy and heading date in rice, *Oryza sativa L.*, using backcross inbred lines", Theoretical and Applied Genetics, (1998) 96, 997-1003), α-123 which is a glutelin-deficient line (Iida, S. et al., "Mutants lacking glutelin subunits in rice: Mapping and combination of mutated glutelin genes", Theoretical and Applied Genetics (1997) 94, 177-183), and Lgc-1 (Kusaba, M. et al., "Low glutelin content1: A dominant mutation that suppresses the glutelin multigene family via RNA silencing in rice", Plant Cell (2003) 15, 1455-1467) were tested.

Table 1 is a list of the 48 tested rice accessions obtained from the National Institute of Agrobiological Sciences Genebank, and the numbers (No) correspond to the numbers indicated in FIG. 1.

TABLE 1

| No | ACCESSION |
|---|---|
| 1 | Yoneshiro |
| 2 | Shomokita |
| 3 | Hatsukogane |
| 4 | Kochihibiki |
| 5 | Suweon 258 |
| 6 | Guizhao 2 |
| 7 | Dunghan Shali |
| 8 | Tannemochi |
| 9 | India Dular |
| 10 | Fukei 158 |
| 11 | Kantou Mochi 157 |
| 12 | Kantou Mochi 160 |
| 13 | Kantou Mochi 164 |
| 14 | Fukei 161 |
| 15 | Fukei 163 |
| 16 | Babutong |
| 17 | Taichung Native 1 |
| 18 | Guangluai 4 |
| 19 | Erjiuqing |
| 20 | Nanjing 11 |
| 21 | Dourado |
| 22 | IAC25 |
| 23 | Pratao Precoce |
| 24 | Niaw Sampa Tong |
| 25 | IR24 |
| 26 | Asominori |
| 27 | Wataribune 2 |
| 28 | Wataribune 3 |
| 29 | Kaohsiung 139 |
| 30 | Saturn |
| 31 | Dawn |
| 32 | Nga Cheik |
| 33 | Toro |
| 34 | Shinriki |

TABLE 1-continued

| No | ACCESSION |
|---|---|
| 35 | Funakiomachi |
| 36 | Shigawatarifune 6 |
| 37 | Kiryouyoshi |
| 38 | Habiganj Boro 2 |
| 39 | Dourado Agulha |
| 40 | Nan-Ei |
| 41 | Azucena |
| 42 | BPI 76 |
| 43 | Raminad Strain 3 |
| 44 | Siam 29 |
| 45 | Bomba |
| 46 | Bomba |
| 47 | H501 |
| 48 | H501 |

Proteins were extracted from mature seeds of the above-mentioned 48 rice cultivars, and the seed protein compositions were analyzed using SDS-PAGE.

Rice seed proteins were extracted by grinding a single mature seed using a multi-beads shocker, and then vigorously stirring for two hours in 600 μL of a protein extraction buffer [50 mM Tris-HCl (pH6.8), 4% SDS, 8 M urea, 5% 2-mercaptoethanol, 20% glycerol], followed by centrifugation and then collection of the supernatant.

As a result, two bands clearly showed polymorphisms of the cultivars (FIG. 1). The first one is the band around 60 kDa (arrow head) and thought to be the WAXY protein because it is lost in the *Japonica cultivars* and strongly expressed in the *Indica cultivars* (Sano, Y. et al., "Genetic-studies of speciatioin in cultivated rice 5. Interspecific and intraspecific differentiation in the WAXY gene-expression of rice", Euphytica (1986) 35, 1-9). The second one is the band around 28 kDa (arrow) immediately below the glutelin acidic subunit. Its electrophoretic mobility in most *Japonica cultivars* was slow compared to that in the *Indica cultivars*. However, of the *Japonica cultivars*, Wataribune 2, Wataribune 3, Funakiomachi, and Shigawatarifune 6 showed bands of nearly the same size as those of the *Indica cultivars* (FIG. 1).

Figure 2:
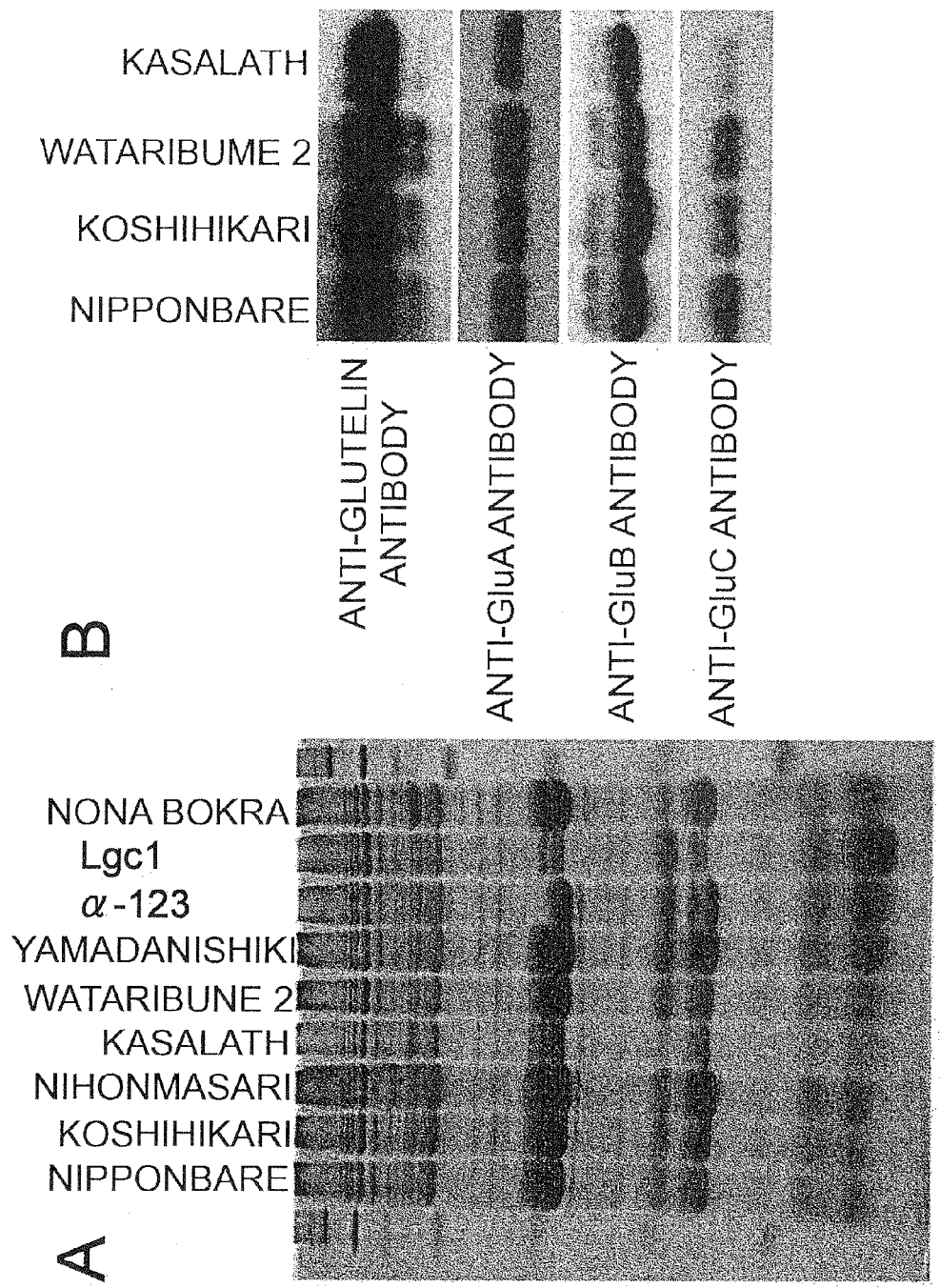
FIG. 2 shows photographs indicating that the band near 28 kDa is a novel glutelin protein. (A) The seed protein composition of α-123 and Lgc-1 which are glutelin-lowering lines were investigated using SDS-PAGE. (B) The seed proteins of Nipponbare, Koshihikari, Wataribune 2, and Kasalath were detected by performing SDS-PAGE followed by Western blotting using an anti-glutelin antibody, anti-GluA antibody, anti-GluB antibody, and anti-GluC antibody.

This band was observed in α-123 which is deficient in GluA-1, GluA-2, and GluB-4, and lost in Lgc-1 which is deficient in all glutelins, suggesting that this band around 28 kDa may be a novel glutelin protein besides GluA-1, GluA-2, and GluB-4 (FIG. 2A).

Therefore, an anti-glutelin antibody which detects all glutelins, anti-GluA antibody, anti-GluB antibody, and anti-GluC antibody were used in Western blotting.

Western blotting was performed by electrophoretically transferring an SDS-PAGE gel onto a PVDF membrane. Primary antibody reactions with each of the glutelin-specific antibodies were carried out by incubating the PVDF membrane in a blocking buffer (5% skim milk-containing TBS-T [25 mM Tris-HCL (pH7.5), 150 mM NaCl, and 0.05% Tween 20]) for one hour, followed by addition of the primary antibodies and incubation for two hours. Secondary antibody reactions were performed by washing with TBS-T and then incubating for one hour in the blocking buffer containing the secondary antibody. Detection was carried out after washing with TBS-T by using the ECL detection kit (GE Healthcare) according to the instructions.

As a result, this band near 28 kDa was detected only with the anti-glutelin antibody (FIG. 2B). This showed that the band near 28 kDa which demonstrates varietal polymorphism is from a novel glutelin.

Example 2

Mapping of the Novel Glutelin Gene

Proteins were extracted from mature seeds of each of the lineages, Koshihikari/Nona Bokra CSSLs and Nipponbare/Kasalath BILs, the polymorphism of the novel glutelin protein was analyzed by SDS-PAGE and compared with the reported genotypes.

Figure 3:
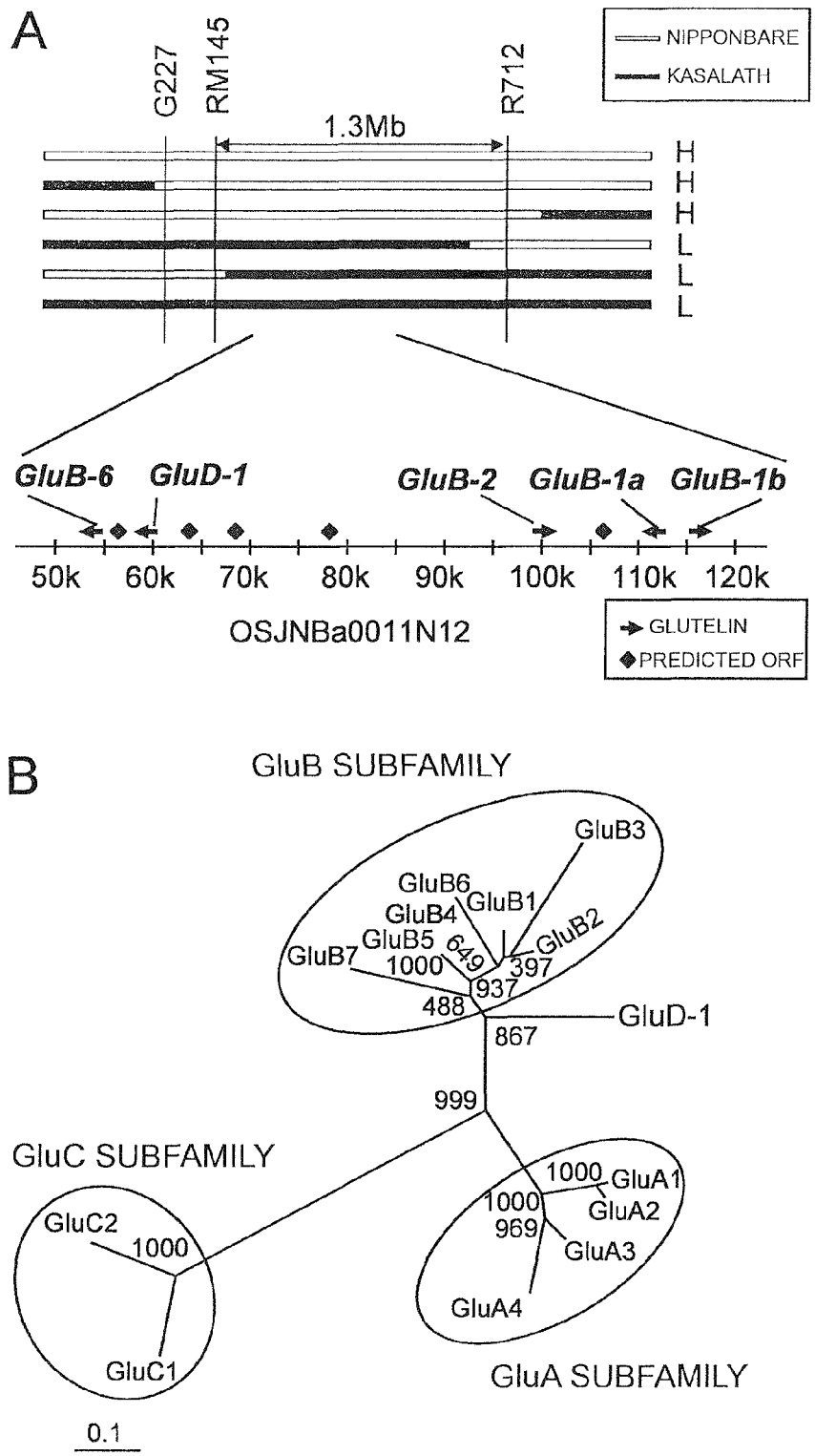
FIG. 3 depicts the mapping of genes encoding the novel glutelin protein near 28 kDa, and the lineage relationship of rice glutelins. (A) By comparing the reported genotype and the phenotype, the region of the locus was narrowed down to within 1.3 Mb. (B) A phylogenic tree was constructed using the full amino acid sequence of glutelin.

As a result, the novel glutelin gene was found to be located within the approximately 1.3 Mb positioned between markers RM145 and R712 on chromosome 2 (FIG. 3A).

The nucleotide sequence of each of the glutelin genes, GluA-2, GluB-1, and GluC-1 was used as the query to perform BLAST searches. The results showed that 15 glutelin genes exist in the rice genome (Table 2).

Table 2 is a list of rice glutelin genes. The located chromosomes, RAP loci, and accession numbers are indicated.

TABLE 2

| GENE | LOCATED CHROMOSOME | RAP LOCUS | ACCESSION NO |
|---|---|---|---|
| GluA-1 | 1 | Os01g0762500 | M17513, X05662, X05661 |
| GluA-2 | 10 | Os10g0400200 | AK107314, X05664, X06149, X05663 |
| GluA-3 | 3 | Os03g0427300 | AK107271, M28159 |
| GluA-4 | 1 | — | — |
| GluB-1a | 2 | Os02g0249800 | AK107343, X14568 |
| GluB-1b | 2 | Os02g0249900 | X15833 |
| GluB-2 | 2 | Os02g0249600 | X54192 |
| GluB-3 | 2 | — | X54193 |
| GluB-4 | 2 | Os02g0268300 | X14393 |
| GluB-5 | 2 | Os02g0268100 | AK107238 |
| GluB-6 | 2 | Os02g0248800 | AY429651 |
| GluB-7 | 2 | Os02g0242600 | AY196923 |
| GluC-1 | 2 | Os02g0453600 | AK064478 |
| GluC-2 | 2 | Os02g0456100 | — |
| GluD-1 | 2 | Os02g0249000 | AY429650 |

The amino acid sequences of 15 rice glutelin genes obtained by BLAST search were subjected to multiple alignment using ClustalW (http://clustalw.ddbj.nig.ac.jp/top-j.html).

A phylogenic tree was constructed using the amino acid sequences. The phylogenic tree was constructed using the neighbor-joining method, and was drawn using the TreeView software (http://taxonomy.zoology.gla.ac.uk/rod/treeview.html).

As a result, the 15 glutelins could be classified into four subfamilies, GluA, GluB, GluC, and GluD (FIG. 3B). Five glutelin genes, GluB-1a, GluB-1b, GluB-2, GluB-6, and GluD-1 were found to be located within 1.3 Mb.

The novel glutelin protein was considered not to be GluB-1a, GluB-1b, or GluB-2 because it was not recognized by the anti-GluB antibodies. Therefore, the nucleotide sequences of GluB-6 and GluD-1 were compared between Nipponbare and Wataribune 2. The coding region of the nucleotide sequence of GluB-6 matched completely, while an SNP (A173T) that causes an amino acid substitution (aspartic acid [Nipponbare] to valine [Wataribune 2]) was found in the acidic subunit coding region of GluD-1 (asterisk in FIG. 4). This SNP was conserved in the GluD-1 nucleotide sequences of Kasalath and Nona Bokra (asterisk in FIG. 4).

Example 3

Identification of GluD-1

An anti-GluD-1 antibody was produced and used in Western blotting to test the seed proteins of Nipponbare, Koshihikari, Kasalath, and Wataribune 2. As a result, a band with slow electrophoretic mobility was detected in Nipponbare and Koshihikari, and a band with fast electrophoretic mobility was detected in Kasalath and Wataribune 2, and polymorphisms were detected by CBB staining (FIG. 5).

The acidic subunits of Nipponbare-type GluD-1 and Wataribune 2-type GluD-1 were expressed in *E. coli*. For protein expression in *E. coli*, the regions encoding the acidic subunits of GluD-1 of Nipponbare and Wataribune 2 were cloned into pET15b (Novagen), and they were used to transform *E. coli* BL21(DE3). After culturing at 37° C. for 12 hours using the Overnight Express system (Novagen), pellets were collected by centrifugation. Suspension in 100 µL of protein extraction buffer was followed by incubation in boiling water for ten minutes, and then this was used in SDS-PAGE and Western blotting.

Figure 5:
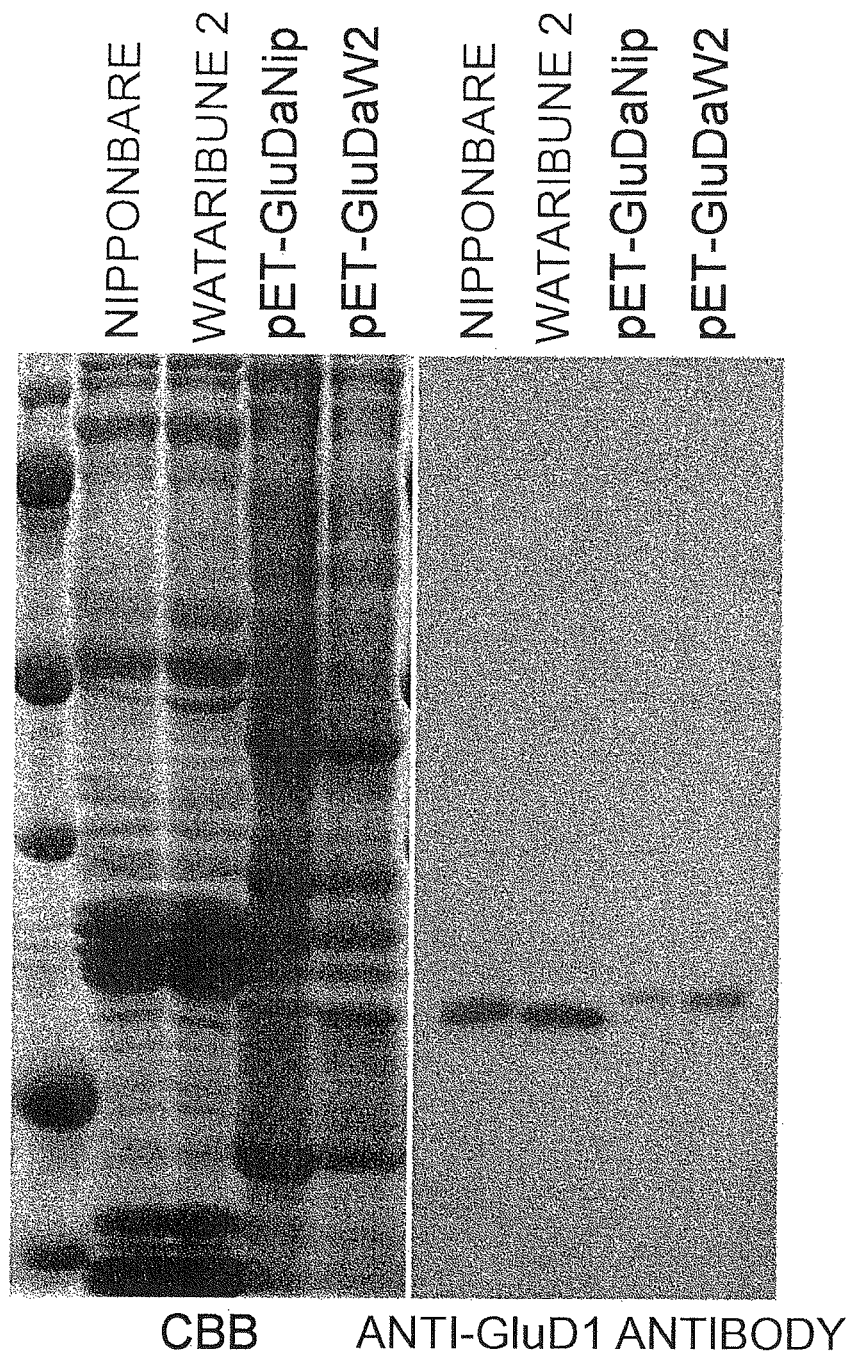
FIG. 5 shows photographs indicating that the novel glutelin protein is GluD-1. The photograph on the left is the result of SDS-PAGE followed by CBB staining, and the photograph on the right is the result of Western blotting and then detection with an anti-GluD-1 antibody. Starting from the left, they are the seed proteins of Nipponbare, the seed proteins of Wataribune 2, the Nipponbare-type GluD-1 acidic subunit expressed in *Escherichia coli*, and the Wataribune 2-type GluD-1 acidic subunit expressed in *E. coli*.

The result shows that the size was nearly the same as that detected by CBB staining and Western blotting (FIG. 5). It is slightly larger than that of the seed proteins because the signal peptide is not cleaved in *E. coli*. The above proved that the novel glutelin gene is encoded by GluD-1.

Example 4

Expression Pattern of GluD-1

Organ-specific expression of GluD-1 was investigated by RT-PCR.

Extraction of total RNA from the root, shoot apex, leaf blade, flower, and callus was performed using a Trizol reagent (Invitrogen) according to the instructions. Extraction of total RNA from seeds 5, 10, 15, 20, and 30 days after flowering was carried out according to the method of Takaiwa et al. (Takaiwa, F. et al., "A rice glutelin gene family—A major type of glutelin messenger-RNAs can be divided into two classes", Molecular & General Genetics, (1987) 208, 15-22).

Reverse transcription of total RNA was performed after DNase I (Takara) treatment using an oligo dT primer and SuperScript III (Invitrogen). For the amplification of ACTIN, the primer set of 5'-TCCATCTTGGCATCTCTCAG-3' (SEQ ID NO: 4) and 5'-GTACCCGCATCAGGCATCTG-3' (SEQ ID NO: 5) was used, and for the amplification of GluD-1, the primer set of 5'-GGATTGACTTTTCCTGGTTGCC-3' (SEQ ID NO: 6) and 5'-TTACTCTTGCAGCACCCATTCC-3' (SEQ ID NO: 7) was used.

Figure 6:
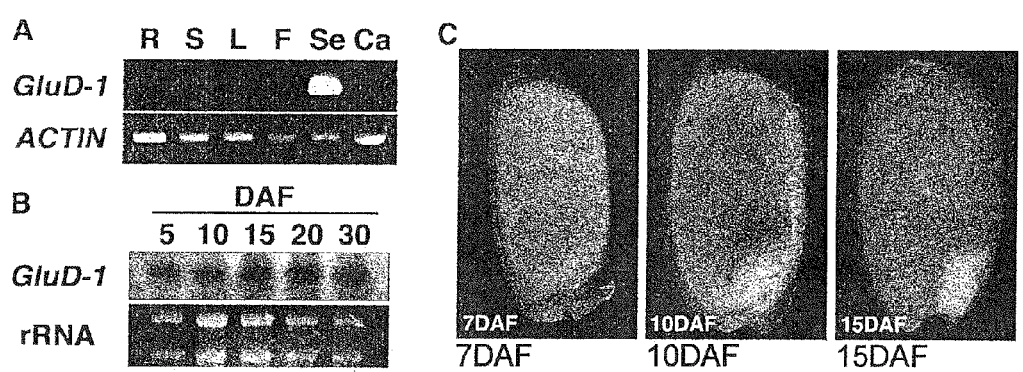
FIG. 6 shows photographs indicating the expression patterns of GluD-1. (A) shows photographs indicating that GluD-1 is expressed specifically in seeds. cDNAs obtained by reverse transcription of total RNAs extracted from the root, near the shoot apex, leaf blade, flower, seed 15 days post-flowering, and callus of rice were used as templates in PCR. As an internal standard, PCR of the ACTIN gene was also carried out. Electrophoresis was followed by ethidium bromide staining and detection under a UV lamp. (B) shows photographs indicating changes in the expression intensity of GluD-1 during the ripening process. Total RNAs extracted from seeds 5, 10, 15, 20, and 30 days post-flowering were subjected to electrophoresis, and Northern blot detection after the internal standard ribosomal RNA is detected. (C) shows photographs indicating the site of GUS expression specific to the tissues inside a seed, which is induced by the GluD-1 promoter. After the seeds of transgenic bodies were manually cut longitudinally 5, 7, and 15 days post-flowering as shown from the left, they were incubated in an X-Gluc solution and then detected.

As a result, GluD-1 was found to be expressed only in the seeds, but not in the root, shoot apex, leaves, flowers, or calli (FIG. 6A).

Next, the time-dependent expression pattern in a ripening seed was investigated by Northern blotting. Northern blotting was carried out by electrophoresing 2 µg of total RNA in 1.2% agarose gel, then capillary blotting onto Hybond N+ (GE Healthcare), and fixing under a UV lamp. Detection was performed using AIPhos Direct (GE Healthcare).

As a result, unlike the other glutelin genes reported so far, the expression gradually increased from the early ripening stage to the late ripening stage without reaching a peak at 10 to 15 days after flowering (FIG. 6B).

Next, to investigate the spatial expression pattern in seeds, approximately 1.7 kb upstream of the GluD-1 coding region (−1,679 to −25 bp) was amplified by PCR from a rice genomic DNA (*cultivar:* Kitaake), and this was cloned into pGPTV-HPT upstream of the GUS gene. The produced construct was used for transformation of rice (cultivar: Kitaake) by the *Agrobacterium* method.

The seeds were cut longitudinally 7, 10, and 15 days after flowering of the transformant with a razor blade and then incubated in 50 mM phosphate buffer containing 0.5 mM 5-bromo-4-chloro-3-indolyl-β-glucuronide (X-Gluc) and 20% methanol to detect GUS. As a result, GUS was not expressed in the germ, but only expressed in the albumen (FIG. 6C). In the seed seven days post-flowering, GUS was expressed only in the endosperm, and not in the aleurone or subaleurone layers (FIG. 6C). At ten days post-flowering, the GUS-expressing region in the seed expanded, but still the expression was only in the endosperm (FIG. 6C). At 15 days post-flowering, GUS expression was observed in the whole albumen including the aleurone and subaleurone layers, but expression in the germ was not observed (FIG. 6C).

From the above, the GluD-1 promoter was considered to be a promoter that induces expression specifically in the endosperm of a seed.

Example 5

Activity of the GluD-1 Promoter

Four seeds from each of the ten strains of transformant seeds were rapidly frozen in liquid nitrogen at 17 days post-flowering, then ground using a multi-beads shocker (Yasui Kikai). This was suspended in a GUS extraction buffer (10 mM 2-mercaptoethanol, 10 mM EDTA, 0.1% SDS, 50 mM phosphate buffer containing 0.1% Triton X-100). After centrifugation, 10 µL of the supernatant and 90 µL of 1 mM 4-methyl-umbelliferyl-β-D-glucuronide (4MUG) were mixed and incubated at 37° C. for one hour. The reaction was stopped with 900 µL of 0.2 M disodium carbonate, and GUS activity was measured using a plate reader (Beckman DTX880). A dilution series of 4-methylumbelliferon (4MU) was used as standard samples. In addition, a dilution series of bovine serum albumin was used as standard samples for measuring the amount of soluble protein by a plate reader (Beckman DTX880) in the Bradford method. The promoter activity was calculated and standardized as GUS activity relative to the amount of soluble protein.

As a result, the GluD-1 promoter activity in a seed was 4.1±3.3 pmoles/µg protein/min. By contrast, the GluD-1 promoter activity was not detected in leaves in the vegetative growth stage (less than 0.001 pmoles/µg protein/min). Although the GluD-1 promoter activity was lower than the Glb-1 promoter activity which induces expression in the endosperm (4.1 versus 43.5 pmoles/µg protein/min; Wu et al., Plant Cell Physiol (1998) 39, 885-889), the Glb-1 promoter is known to induce expression even in leaves in the vegetative growth stage. So far, the RAG-1 (16 kDa allergen) promoter has been reported as an endosperm-specific promoter, but the GluD-1 promoter was very strong in comparison to this (4.1 versus 0.9 pmoles/µg protein/min; Wu et al., Plant Cell Physiol. (1998) 39, 885-889).

The invention claimed is:

1. A construct comprising a nucleotide sequence consisting of (a) or (b) below, which has promoter activity:
   (a) the nucleotide sequence of SEQ ID NO:3;
   (b) a nucleotide sequence having 98% or more sequence identity to the nucleotide sequence of SEQ ID NO:3.

2. The construct of claim 1, which has promoter activity specific to the endosperm of a plant.

3. The construct of claim 2, wherein the plant accumulates a seed storage protein.

4. A DNA having a structure in which an exogenous gene is operably linked downstream of the construct of claim 1.

5. A vector comprising the construct of claim 1.

6. A transformed plant cell comprising the construct, of claim 1.

7. A transformed plant comprising the transformed plant cell of claim 6.

8. A transformed plant which is a progeny or clone of the transformed plant of claim 7 wherein the progeny or clone comprises the construct of claim 1.

9. A reproductive material of the transformed plant of claim 7.

10. A method for expressing an exogenous gene specifically in an endosperm of a plant, which comprises introducing into a plant cell the construct of claim 1 and regenerating a plant from the plant cell.

11. The method of claim 10, wherein the plant accumulates a seed storage protein.

12. A plant obtained by the method of claim 10, or a seed thereof.

13. An agent for inducing expression of an exogenous gene specifically in an endosperm of a plant, which comprises as an active ingredient,
   the construct of claim 1.

14. An agent for inducing accumulation of an exogenous protein specifically in an endosperm of a plant, which comprises as an active ingredient,
   the construct of claim 1.

15. A transformed plant cell comprising the vector of claim 5.

16. A transformed plant comprising the transformed plant cell of claim 15.

17. A transformed plant which is a progeny or clone of the transformed plant of claim 16 wherein the progeny or clone comprises the construct of claim 1.

18. A reproductive material of the transformed plant of claim 16.

19. A method for producing a transformed plant, which comprises introducing into a plant cell the construct of claim 1.

20. A method for producing a transformed plant, which comprises introducing into a plant cell the vector of claim 5.

21. A method for expressing an exogenous gene specifically in an endosperm of a plant, which comprises introducing into a plant cell the vector of claim 5 and regenerating a plant from the plant cell.

22. The method of claim 21, wherein the plant accumulates a seed storage protein.

23. An agent for inducing expression of an exogenous gene specifically in an endosperm of a plant, which comprises as an active ingredient,
   the vector of claim 5.

24. An agent for inducing accumulation of an exogenous protein specifically in an endosperm of a plant, which comprises as an active ingredient,
   the vector of claim 5.

* * * * *

SEQUENCE LISTING

<160> NUMBER OF SEQ ID NOS: 11

<210> SEQ ID NO 1
<211> LENGTH: 1455
<212> TYPE: DNA
<213> ORGANISM: Oryza sativa

<400> SEQUENCE: 1

```
atggcaacta ctacctctct attgtcttcc tgtctctgtg ctcttctctt ggctccgctc      60
tttagccaag gtgtagatgc atgggaaagc cgacaagggg cttccaggca gtgcagattt     120
gataggttac aagcatttga gcccctaaga aaggtacgat cggaagctgg ggacacagag     180
tactttgatg agagaaatga gcagtttcga tgcgctggtg tctttgtcat tcggcgcgtg     240
attgagccac aaggccttgt ggtgcctcga tactcgaaca ctcctgctct agcctacata     300
atccaaggaa aaggttacgt aggattgact tttcctggtt gcccagcaac acaccaacaa     360
caattccaac tatttgaaca aagacagagc gaccaagctc ataagtttag agatgagcac     420
cagaagattc acgaatttag caaggggat gttgttgcac ttccggctag tgttgcacat     480
tggttctaca atggtggtga tacaccggct gttgttgtct atgtttatga cataaaaagt     540
tttgctaatc agcttgaacc aaggcagaag gagttttat tagctggtaa caaccagaga     600
gggcaacaaa tatttgaaca ttccatcttt caacactctg acaaaatat atttagtggg     660
ttcaatactg aggtacttag cgaggcccctt ggaataaaca cggaggcttc aagaggctc      720
caaagtcaaa atgaccaaag gggagatatc attcgagtga agcacgggct tcaattgttg     780
aaacccacat taacacaacg acaggaagaa catcgtcaat atcaacaagt ccagtatcgt     840
gaaggacaat ataatggatt ggacgagaat ttctgtacaa taaaggcaag ggtaaacatt     900
gaaaatccta gccgcgctga ctactacaac cctcgtgctg aaggataac ccttcttaac      960
aaccaaaagt tccctattct caaccttatt ggaatgggtg ctgcaagagt aaacttatac    1020
cagaatgctc ttctctcacc cttctggaac attaatgccc atagtgtagt gtatatcatc    1080
caaggaagtg tgcgagtaca ggttgccaat aatcaaggaa gatctgtgtt taatggtgta    1140
cttcatcagg ggcaactatt aatcatacca caaaaccatg ccgtcattaa gaaagccgag    1200
cacaatgggt gccagtatgt cgcaataaag acaatttcgg accctacggt gagttgggtt    1260
gctggaaaga actccatatt acgtgcattg cctgtagatg ttattgccaa tgcttatcgt    1320
atctcgaggg atgaagcccg acgtctaaag aataataggg cagatgagat tggccctttt    1380
actcctcgtt tccccccagaa gagccagcgg ggttaccagt tcctaactga aggcctctct    1440
ttaatcggca tgtaa                                                     1455
```

<210> SEQ ID NO 2
<211> LENGTH: 484
<212> TYPE: PRT
<213> ORGANISM: Oryza sativa

<400> SEQUENCE: 2

```
Met Ala Thr Thr Thr Ser Leu Leu Ser Ser Cys Leu Cys Ala Leu Leu
1               5                   10                  15

Leu Ala Pro Leu Phe Ser Gln Gly Val Asp Ala Trp Glu Ser Arg Gln
            20                  25                  30

Gly Ala Ser Arg Gln Cys Arg Phe Asp Arg Leu Gln Ala Phe Glu Pro
        35                  40                  45

Leu Arg Lys Val Arg Ser Glu Ala Gly Asp Thr Glu Tyr Phe Asp Glu
```

```
            50                  55                  60
Arg Asn Glu Gln Phe Arg Cys Ala Gly Val Phe Val Ile Arg Arg Val
65                  70                  75                  80

Ile Glu Pro Gln Gly Leu Val Val Pro Arg Tyr Ser Asn Thr Pro Ala
                85                  90                  95

Leu Ala Tyr Ile Ile Gln Gly Lys Gly Tyr Val Gly Leu Thr Phe Pro
                100                 105                 110

Gly Cys Pro Ala Thr His Gln Gln Phe Gln Leu Phe Glu Gln Arg
            115                 120                 125

Gln Ser Asp Gln Ala His Lys Phe Arg Asp Glu His Gln Lys Ile His
130                 135                 140

Glu Phe Arg Gln Gly Asp Val Val Ala Leu Pro Ala Ser Val Ala His
145                 150                 155                 160

Trp Phe Tyr Asn Gly Gly Asp Thr Pro Ala Val Val Tyr Val Tyr
                165                 170                 175

Asp Ile Lys Ser Phe Ala Asn Gln Leu Glu Pro Arg Gly Lys Glu Phe
                180                 185                 190

Leu Leu Ala Gly Asn Asn Gln Arg Gly Gln Gln Ile Phe Glu His Ser
                195                 200                 205

Ile Phe Gln His Ser Gly Gln Asn Ile Phe Ser Gly Phe Asn Thr Glu
210                 215                 220

Val Leu Ser Glu Ala Leu Gly Ile Asn Thr Glu Ala Ser Lys Arg Leu
225                 230                 235                 240

Gln Ser Gln Asn Asp Gln Arg Gly Asp Ile Ile Arg Val Lys His Gly
                245                 250                 255

Leu Gln Leu Leu Lys Pro Thr Leu Thr Gln Arg Gln Glu Glu His Arg
                260                 265                 270

Gln Tyr Gln Gln Val Gln Tyr Arg Glu Gly Gln Tyr Asn Gly Leu Asp
                275                 280                 285

Glu Asn Phe Cys Thr Ile Lys Ala Arg Val Asn Ile Glu Asn Pro Ser
290                 295                 300

Arg Ala Asp Tyr Tyr Asn Pro Arg Ala Gly Arg Ile Thr Leu Leu Asn
305                 310                 315                 320

Asn Gln Lys Phe Pro Ile Leu Asn Leu Ile Gly Met Gly Ala Ala Arg
                325                 330                 335

Val Asn Leu Tyr Gln Asn Ala Leu Leu Ser Pro Phe Trp Asn Ile Asn
                340                 345                 350

Ala His Ser Val Val Tyr Ile Ile Gln Gly Ser Val Arg Val Gln Val
                355                 360                 365

Ala Asn Asn Gln Gly Arg Ser Val Phe Asn Gly Val Leu His Gln Gly
                370                 375                 380

Gln Leu Leu Ile Ile Pro Gln Asn His Ala Val Ile Lys Lys Ala Glu
385                 390                 395                 400

His Asn Gly Cys Gln Tyr Val Ala Ile Lys Thr Ile Ser Asp Pro Thr
                405                 410                 415

Val Ser Trp Val Ala Gly Lys Asn Ser Ile Leu Arg Ala Leu Pro Val
                420                 425                 430

Asp Val Ile Ala Asn Ala Tyr Arg Ile Ser Arg Asp Glu Ala Arg Arg
                435                 440                 445

Leu Lys Asn Asn Arg Ala Asp Glu Ile Gly Pro Phe Thr Pro Arg Phe
                450                 455                 460

Pro Gln Lys Ser Gln Arg Gly Tyr Gln Phe Leu Thr Glu Gly Leu Ser
465                 470                 475                 480
```

Leu Ile Gly Met

<210> SEQ ID NO 3
<211> LENGTH: 1651
<212> TYPE: DNA
<213> ORGANISM: Oryza sativa

<400> SEQUENCE: 3

| | | | | | |
|---|---|---|---|---|---|
| tttggaccct | aagtttaatc | ttgtattggg | ccttgggcca | agatagaat | aaaaatccaa | 60 |
| aagatataga | aggtgggaag | catagaagta | atggaggtaa | gctgacatct | cgaatttttt | 120 |
| ggtttgtttg | atttcttggg | caacaaccga | acagaaaccc | gaagaccaat | ctagccaaaa | 180 |
| acaaaagcca | aagagggcac | tgaagactga | agaaatcgat | acatcaggtc | agttcggctt | 240 |
| ggttttgttc | agtcttttcag | tgctcagcga | ttttttcgtcc | actccactttt | tgtttttta | 300 |
| ttagagtgaa | tatattaatt | caaacgatta | cactacgctt | cgcctgcaca | aacctaggag | 360 |
| ccctagagga | taatatggaa | gaatacacag | gtgtatacaa | agaagagaat | gcaaaggcat | 420 |
| cataaccttg | ttagctaagt | ggcttagaaa | actggaagct | ggtgcttggc | tttatcttttt | 480 |
| ttctatagaa | agactacaca | tgctattgaa | ccatatgaac | cacatagttt | tctcataaac | 540 |
| cggacaatta | aagagtgtgt | tctttgagag | tgaggatgaa | ctgttggtga | gtctctatgg | 600 |
| aaattaactc | atctggatcc | aaactttgtc | ccatctcaaa | tccacttatt | cctcttagga | 660 |
| tatagaaatt | ttcttgagac | cgcacacatg | acttagcgta | aatatagcaa | acttcctatt | 720 |
| ctcttatgaa | ttgagctatg | actaccttca | ctctttatag | tacagtgaat | ataaagtaag | 780 |
| tcatattcta | tttatacact | catttgttgt | gccaaactag | taatcaatta | gagtcattgt | 840 |
| ctttatctttt | gctcatcgaa | gaacacatta | taattctctt | tatggacaaa | tcatggtaac | 900 |
| atattcaact | accgagggcc | taactctcct | tgcacactta | gaaaatatga | ttagtcttaa | 960 |
| taatctatgt | tgtctttaat | caccaagact | caaataaagg | gtctagatgt | gtaaacgaa | 1020 |
| gagctaattg | caaactaacc | aacaaaaacc | atatatttt | tttctcttga | tgtttactta | 1080 |
| atctaactaa | aagcgacttt | agtagtttgg | acaatttgat | gatccattaa | agttttaga | 1140 |
| tatgaccaca | cctcgtaggt | atacaagagt | cgcaaatatt | tatcagctaa | taaaaagtac | 1200 |
| caaaagtaag | atatgcttga | aaacaacaga | taatgatgta | actggtcaag | cttaagtaaa | 1260 |
| tggattaata | caggttacaa | agttgttgaa | gaaacaaaca | agtctatcaa | cttttttgatt | 1320 |
| gcttgtaaaa | ctttgtaaag | tacaaaagaa | gaaagagtat | acacaaaaat | gctagaagct | 1380 |
| aacaagtttg | ttgttgcaaa | agaacactta | atgcatttgg | ctagaaactt | tatgagaaaa | 1440 |
| tgaacacatt | tggcatgtac | gaaacacgtc | aaaaagtata | tggtatgaat | catttcaaca | 1500 |
| acatcctttg | atgtagtgac | ttctttggac | caaaaatctt | gcattgtaca | caatccttgt | 1560 |
| ccacaggtta | acaaacttca | taagcacctt | ggatcccaaa | gccactttta | ttggctataa | 1620 |
| aaaccaccac | ctacgcactt | gcaatcacat | c | | | 1651 |

<210> SEQ ID NO 4
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 4
tccatcttgg catctctcag                                                    20

<210> SEQ ID NO 5

-continued

```
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 5
gtacccgcat caggcatctg                                                      20

<210> SEQ ID NO 6
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 6
ggattgactt ttcctggttg cc                                                   22

<210> SEQ ID NO 7
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 7
ttactcttgc agcacccatt cc                                                   22

<210> SEQ ID NO 8
<211> LENGTH: 484
<212> TYPE: PRT
<213> ORGANISM: Oryza sativa

<400> SEQUENCE: 8

Met Ala Thr Thr Thr Ser Leu Leu Ser Ser Cys Leu Cys Ala Leu Leu
1               5                   10                  15

Leu Ala Pro Leu Phe Ser Gln Gly Val Asp Ala Trp Glu Ser Arg Gln
                20                  25                  30

Gly Ala Ser Arg Gln Cys Arg Phe Asp Arg Leu Gln Ala Phe Glu Pro
            35                  40                  45

Leu Arg Lys Val Arg Ser Glu Ala Gly Asp Thr Glu Tyr Phe Asp Glu
        50                  55                  60

Arg Asn Glu Gln Phe Arg Cys Ala Gly Val Phe Val Ile Arg Arg Val
65                  70                  75                  80

Ile Glu Pro Gln Gly Leu Val Val Pro Arg Tyr Ser Asn Thr Pro Ala
                85                  90                  95

Leu Ala Tyr Ile Ile Gln Gly Lys Gly Tyr Val Gly Leu Thr Phe Pro
                100                 105                 110

Gly Cys Pro Ala Thr His Gln Gln Phe Gln Leu Phe Glu Gln Arg
            115                 120                 125

Gln Ser Asp Gln Ala His Lys Phe Arg Asp Glu His Gln Lys Ile His
        130                 135                 140

Glu Phe Arg Gln Gly Asp Val Val Ala Leu Pro Ala Ser Val Ala His
145                 150                 155                 160

Trp Phe Tyr Asn Gly Gly Asp Thr Pro Ala Val Val Val Tyr Val Tyr
                165                 170                 175

Asp Ile Lys Ser Phe Ala Asn Gln Leu Glu Pro Arg Gln Lys Glu Phe
                180                 185                 190

Leu Leu Ala Gly Asn Asn Gln Arg Gly Gln Gln Ile Phe Glu His Ser
            195                 200                 205
```

Ile Phe Gln His Ser Gly Gln Asn Ile Phe Ser Gly Phe Asn Thr Glu
            210                 215                 220

Val Leu Ser Glu Ala Leu Gly Ile Asn Thr Glu Ala Ser Lys Arg Leu
225                 230                 235                 240

Gln Ser Gln Asn Asp Gln Arg Gly Asp Ile Ile Arg Val Lys His Gly
                245                 250                 255

Leu Gln Leu Leu Lys Pro Thr Leu Thr Gln Arg Gln Glu His Arg
            260                 265                 270

Gln Tyr Gln Gln Val Gln Tyr Arg Glu Gly Gln Tyr Asn Gly Leu Asp
            275                 280                 285

Glu Asn Phe Cys Thr Ile Lys Ala Arg Val Asn Ile Glu Asn Pro Ser
290                 295                 300

Arg Ala Asp Tyr Tyr Asn Pro Arg Ala Gly Arg Ile Thr Leu Leu Asn
305                 310                 315                 320

Asn Gln Lys Phe Pro Ile Leu Asn Leu Ile Gly Met Gly Ala Ala Arg
                325                 330                 335

Val Asn Leu Tyr Gln Asn Ala Leu Leu Ser Pro Phe Trp Asn Ile Asn
            340                 345                 350

Ala His Ser Val Val Tyr Ile Ile Gln Gly Ser Val Arg Val Gln Val
            355                 360                 365

Ala Asn Asn Gln Gly Arg Ser Val Phe Asn Gly Val Leu His Gln Gly
370                 375                 380

Gln Leu Leu Ile Ile Pro Gln Asn His Ala Val Ile Lys Lys Ala Glu
385                 390                 395                 400

His Asn Gly Cys Gln Tyr Val Ala Ile Lys Thr Ile Ser Asp Pro Thr
                405                 410                 415

Val Ser Trp Val Ala Gly Lys Asn Ser Ile Leu Arg Ala Leu Pro Val
            420                 425                 430

Asp Val Ile Ala Asn Ala Tyr Arg Ile Ser Arg Asp Glu Ala Arg Arg
            435                 440                 445

Leu Lys Asn Asn Arg Ala Asp Glu Ile Gly Pro Phe Thr Pro Arg Phe
450                 455                 460

Pro Gln Lys Ser Gln Arg Gly Tyr Gln Phe Leu Thr Glu Gly Leu Ser
465                 470                 475                 480

Leu Ile Gly Met

<210> SEQ ID NO 9
<211> LENGTH: 484
<212> TYPE: PRT
<213> ORGANISM: Oryza sativa

<400> SEQUENCE: 9

Met Ala Thr Thr Thr Ser Leu Leu Ser Ser Cys Leu Cys Ala Leu Leu
1               5                   10                  15

Leu Ala Pro Leu Phe Ser Gln Gly Val Asp Ala Trp Glu Ser Arg Gln
            20                  25                  30

Gly Ala Ser Arg Gln Cys Arg Phe Asp Arg Leu Gln Ala Phe Glu Pro
        35                  40                  45

Leu Arg Lys Val Arg Ser Glu Ala Gly Val Thr Glu Tyr Phe Asp Glu
    50                  55                  60

Arg Asn Glu Gln Phe Arg Cys Ala Gly Val Phe Val Ile Arg Arg Val
65                  70                  75                  80

Ile Glu Pro Gln Gly Leu Val Val Pro Arg Tyr Ser Asn Thr Pro Ala
                85                  90                  95

Leu Ala Tyr Ile Ile Gln Gly Lys Gly Tyr Val Gly Leu Thr Phe Pro
            100                 105                 110

Gly Cys Pro Ala Thr His Gln Gln Phe Gln Leu Phe Glu Gln Arg
        115                 120                 125

Gln Ser Asp Gln Ala His Lys Phe Arg Asp Glu His Gln Lys Ile His
130                 135                 140

Glu Phe Arg Gln Gly Asp Val Ala Leu Pro Ala Ser Val Ala His
145                 150                 155                 160

Trp Phe Tyr Asn Gly Asp Thr Pro Ala Val Val Tyr Val Tyr
                165                 170                 175

Asp Ile Lys Ser Phe Ala Asn Gln Leu Glu Pro Arg Lys Glu Phe
            180                 185                 190

Leu Leu Ala Gly Asn Asn Gln Arg Gly Gln Gln Ile Phe Glu His Ser
        195                 200                 205

Ile Phe Gln His Ser Gly Gln Asn Ile Phe Ser Gly Phe Asn Thr Glu
210                 215                 220

Val Leu Ser Glu Ala Leu Gly Ile Asn Thr Glu Ala Ser Lys Arg Leu
225                 230                 235                 240

Gln Ser Gln Asn Asp Gln Arg Gly Asp Ile Ile Arg Val Lys His Gly
                245                 250                 255

Leu Gln Leu Leu Lys Pro Thr Leu Thr Gln Arg Gln Glu His Arg
        260                 265                 270

Gln Tyr Gln Gln Val Gln Tyr Arg Glu Gly Gln Tyr Asn Gly Leu Asp
            275                 280                 285

Glu Asn Phe Cys Thr Ile Lys Ala Arg Val Asn Ile Glu Asn Pro Ser
290                 295                 300

Arg Ala Asp Tyr Tyr Asn Pro Arg Ala Gly Arg Ile Thr Leu Leu Asn
305                 310                 315                 320

Asn Gln Lys Phe Pro Ile Leu Asn Leu Ile Gly Met Gly Ala Ala Arg
                325                 330                 335

Val Asn Leu Tyr Gln Asn Ala Leu Leu Ser Pro Phe Trp Asn Ile Asn
            340                 345                 350

Ala His Ser Val Val Tyr Ile Ile Gln Gly Ser Val Arg Val Gln Val
        355                 360                 365

Ala Asn Asn Gln Gly Arg Ser Val Phe Asn Gly Val Leu His Gln Gly
370                 375                 380

Gln Leu Leu Ile Ile Pro Gln Asn His Ala Val Ile Lys Lys Ala Glu
385                 390                 395                 400

His Asn Gly Cys Gln Tyr Val Ala Ile Lys Thr Ile Ser Asp Pro Thr
                405                 410                 415

Val Ser Trp Val Ala Gly Lys Asn Ser Ile Leu Arg Ala Leu Pro Val
            420                 425                 430

Asp Val Ile Ala Asn Ala Tyr Arg Ile Ser Arg Asp Glu Ala Arg Arg
        435                 440                 445

Leu Lys Asn Asn Arg Ala Asp Glu Ile Gly Pro Phe Thr Pro Arg Phe
450                 455                 460

Pro Gln Lys Ser Gln Arg Gly Tyr Gln Phe Leu Thr Glu Gly Leu Ser
465                 470                 475                 480

Leu Ile Gly Met

<210> SEQ ID NO 10
<211> LENGTH: 484
<212> TYPE: PRT
<213> ORGANISM: Oryza sativa -continued

```
<400> SEQUENCE: 10

Met Ala Thr Thr Thr Ser Leu Leu Ser Ser Cys Leu Cys Ala Leu Leu
1               5                   10                  15

Leu Ala Pro Leu Phe Ser Gln Gly Val Asp Ala Trp Glu Ser Arg Gln
            20                  25                  30

Gly Ala Ser Arg Glu Cys Arg Phe Asp Arg Leu Gln Ala Phe Glu Pro
        35                  40                  45

Leu Arg Lys Ala Arg Ser Glu Ala Gly Val Thr Glu Tyr Phe Asp Glu
50                  55                  60

Arg Asn Glu Gln Phe Arg Cys Ala Gly Val Phe Val Ile Arg Arg Val
65                  70                  75                  80

Ile Glu Pro Gln Gly Leu Val Val Pro Arg Tyr Ser Asn Thr Pro Ala
                85                  90                  95

Leu Ala Tyr Ile Ile Gln Gly Lys Gly Tyr Val Gly Leu Thr Phe Pro
            100                 105                 110

Gly Cys Pro Ala Thr His Gln Gln Phe Gln Leu Phe Glu Gln Arg
        115                 120                 125

Gln Ser Asp Gln Ala His Lys Phe Arg Asp Glu His Gln Lys Ile His
130                 135                 140

Glu Phe Arg Gln Gly Asp Val Val Ala Leu Pro Ala Ser Val Ala His
145                 150                 155                 160

Trp Phe Tyr Asn Gly Gly Asp Thr Pro Ala Val Val Tyr Val Tyr
                165                 170                 175

Asp Ile Lys Ser Phe Ala Asn Gln Leu Glu Pro Arg Gln Lys Glu Phe
            180                 185                 190

Leu Leu Ala Gly Asn Asn Gln Arg Gly Gln Gln Ile Phe Glu His Ser
195                 200                 205

Ile Phe Gln His Ser Gly Gln Asn Ile Phe Ser Gly Phe Asn Thr Glu
210                 215                 220

Val Leu Ser Glu Ala Leu Gly Ile Asn Thr Glu Ala Ala Lys Arg Leu
225                 230                 235                 240

Gln Ser Gln Asn Asp Gln Arg Gly Asp Ile Ile Arg Val Lys His Gly
                245                 250                 255

Leu Gln Leu Leu Lys Pro Thr Leu Thr Gln Arg Gln Glu Glu Pro Arg
            260                 265                 270

Gln Tyr Gln Gln Val Gln Tyr Arg Glu Gly Gln Tyr Asn Gly Leu Asp
        275                 280                 285

Glu Asn Phe Cys Thr Ile Lys Ala Arg Val Asn Ile Glu Asn Pro Asn
    290                 295                 300

Arg Ala Asp Tyr Tyr Asn Pro Arg Ala Gly Arg Ile Thr Leu Leu Asn
305                 310                 315                 320

Asn Gln Lys Phe Pro Ile Leu Asn Leu Ile Gly Met Gly Ala Ala Arg
                325                 330                 335

Val Asn Leu Tyr Gln Asn Ala Leu Leu Ser Pro Phe Trp Asn Ile Asn
            340                 345                 350

Ala His Ser Val Val Tyr Ile Ile Gln Gly Ser Ala Gln Val Gln Val
        355                 360                 365

Ala Asn Asn Gln Gly Arg Thr Val Phe Ser Gly Val Leu His Gln Gly
    370                 375                 380

Gln Leu Leu Ile Ile Pro Gln Asn His Ala Val Ile Lys Lys Ala Glu
385                 390                 395                 400

His Asn Gly Cys Gln Tyr Val Ala Ile Lys Thr Ile Pro Asn Pro Met
                405                 410                 415
```

```
Val Ser Arg Val Ala Gly Lys Asn Ser Ile Leu Arg Ala Leu Pro Val
            420                 425                 430

Asp Val Ile Ala Asn Ala Tyr Arg Ile Ser Arg Asp Glu Ala Arg Arg
        435                 440                 445

Leu Lys Asn Asn Arg Ala Asp Glu Ile Gly Ala Phe Thr Pro Arg Phe
    450                 455                 460

Pro Gln Lys Ser Gln Arg Gly Tyr Gln Phe Leu Thr Lys Gly Leu Ser
465                 470                 475                 480

Leu Ile Gly Met

<210> SEQ ID NO 11
<211> LENGTH: 484
<212> TYPE: PRT
<213> ORGANISM: Oryza sativa

<400> SEQUENCE: 11

Met Ala Thr Thr Thr Ser Leu Leu Ser Ser Cys Leu Cys Ala Leu Leu
1               5                   10                  15

Leu Ala Pro Leu Phe Ser Gln Gly Val Asp Ala Trp Glu Ser Arg Gln
            20                  25                  30

Gly Ala Ser Arg Glu Cys Arg Phe Asp Arg Leu Gln Ala Phe Glu Pro
        35                  40                  45

Leu Arg Lys Ala Arg Ser Glu Ala Gly Val Thr Glu Tyr Phe Asp Glu
    50                  55                  60

Ile Asn Glu Gln Phe Arg Cys Ala Gly Val Phe Val Ile Arg Arg Val
65                  70                  75                  80

Ile Glu Pro Gln Gly Leu Val Val Pro Arg Tyr Ser Asn Thr Pro Ala
                85                  90                  95

Leu Ala Tyr Ile Ile Gln Gly Lys Gly Tyr Val Gly Leu Thr Phe Pro
            100                 105                 110

Gly Cys Pro Ala Thr His Gln Gln Phe Gln Leu Phe Glu Gln Arg
        115                 120                 125

Gln Ser Asp Gln Ala His Lys Phe Arg Asp Glu His Gln Lys Ile His
    130                 135                 140

Glu Phe Arg Gln Gly Asp Val Val Ala Leu Pro Ala Ser Val Ala His
145                 150                 155                 160

Trp Phe Tyr Asn Gly Gly Asp Thr Pro Ala Val Val Tyr Val Tyr
                165                 170                 175

Asp Ile Lys Ser Phe Ala Asn Gln Leu Glu Pro Arg Gln Lys Glu Phe
            180                 185                 190

Leu Leu Ala Gly Asn Asn Gln Arg Gly Gln Gln Ile Phe Glu His Ser
        195                 200                 205

Ile Phe Gln His Ser Gly Gln Asn Ile Phe Ser Gly Phe Asn Thr Glu
    210                 215                 220

Val Leu Ser Glu Ala Leu Gly Ile Asn Thr Glu Ala Ala Lys Arg Leu
225                 230                 235                 240

Gln Ser Gln Asn Asp Gln Arg Gly Asp Ile Ile Arg Val Lys His Gly
                245                 250                 255

Leu Gln Leu Leu Lys Pro Thr Leu Thr Gln Arg Gln Glu Glu Pro Arg
            260                 265                 270

Gln Tyr Gln Gln Val Gln Tyr Arg Glu Gly Gln Tyr Asn Gly Leu Asp
        275                 280                 285

Glu Asn Phe Cys Thr Ile Lys Ala Arg Val Asn Ile Glu Asn Pro Asn
    290                 295                 300

Arg Ala Asp Tyr Tyr Asn Pro Arg Ala Gly Arg Ile Thr Leu Leu Asn
```

-continued

```
                    305                 310                 315                 320
Asn Gln Lys Phe Pro Ile Leu Asn Leu Ile Gly Met Gly Ala Ala Arg
                325                 330                 335

Val Asn Leu Tyr Gln Asn Ala Leu Leu Ser Pro Phe Trp Asn Ile Asn
                340                 345                 350

Ala His Ser Val Val Tyr Ile Ile Gln Gly Ser Ala Gln Val Gln Val
                355                 360                 365

Ala Asn Asn Gln Gly Arg Thr Val Phe Ser Gly Val Leu His Gln Gly
                370                 375                 380

Gln Leu Leu Ile Ile Pro Gln Asn His Ala Val Ile Lys Lys Ala Glu
385                 390                 395                 400

His Asn Gly Cys Gln Tyr Val Ala Ile Lys Thr Ile Pro Asn Pro Met
                405                 410                 415

Val Ser Arg Val Ala Gly Lys Asn Ser Ile Leu Arg Ala Leu Pro Val
                420                 425                 430

Asp Val Ile Ala Asn Ala Tyr Arg Ile Ser Arg Asp Glu Ala Arg Arg
                435                 440                 445

Leu Lys Asn Asn Arg Ala Asp Glu Ile Gly Ala Phe Thr Pro Arg Phe
                450                 455                 460

Pro Gln Lys Ser Gln Arg Gly Tyr Gln Phe Leu Thr Lys Gly Leu Ser
465                 470                 475                 480

Leu Ile Gly Met
```